United States Patent
Michlitsch et al.

(10) Patent No.: US 9,591,879 B2
(45) Date of Patent: Mar. 14, 2017

(54) METHODS AND APPARATUS FOR EAR PROTECTION

(76) Inventors: Kenneth J. Michlitsch, Livermore, CA (US); Jane P. Bearinger, Livermore, CA (US)

( * ) Notice: Subject to any disclaimer, the term of this patent is extended or adjusted under 35 U.S.C. 154(b) by 689 days.

(21) Appl. No.: 13/168,618

(22) Filed: Jun. 24, 2011

(65) Prior Publication Data
US 2012/0124719 A1 May 24, 2012

Related U.S. Application Data

(60) Provisional application No. 61/417,161, filed on Nov. 24, 2010, provisional application No. 61/434,359, filed on Jan. 19, 2011.

(51) Int. Cl.
| | | |
|---|---|---|
| A61F 11/06 | (2006.01) | |
| A41D 13/05 | (2006.01) | |
| A61F 11/14 | (2006.01) | |
| A45D 44/12 | (2006.01) | |

(52) U.S. Cl.
CPC ............. *A41D 13/05* (2013.01); *A61F 11/14* (2013.01); *A45D 44/12* (2013.01)

(58) Field of Classification Search
CPC ............................... A41D 13/05; A61F 11/14
USPC ...................................................... 2/209, 423
See application file for complete search history.

(56) References Cited

U.S. PATENT DOCUMENTS

| | | |
|---|---|---|
| 190,720 A | 5/1877 | Kleinert |
| 993,620 A | 5/1911 | Quinn |
| 1,697,102 A | 1/1929 | Barrington |
| 2,325,150 A | 7/1943 | Sahlmann |
| 2,378,398 A | 6/1945 | Fiedler |
| 2,439,289 A * | 4/1948 | Fanslow ........................... 2/209 |
| 2,444,251 A | 6/1948 | Goldman |
| 2,582,907 A | 1/1952 | Kaufmann |
| 2,700,162 A * | 1/1955 | Fuller ..................... A61F 11/06 2/209 |
| 2,712,134 A | 7/1955 | Cyr |
| 2,727,245 A | 12/1955 | Suggs |
| 2,768,384 A | 10/1956 | Crane et al. |
| 3,112,493 A | 12/1963 | Greenberg |

(Continued)

*Primary Examiner* — Katherine Moran
(74) *Attorney, Agent, or Firm* — Foley & Lardner LLP; Nicola A. Pisano; Albert K. Heng

(57) ABSTRACT

Methods and apparatus are provided for protecting the external ear from the elements, heat, cold, wind, rain and/or snow. In some embodiments, an ear protector comprises a conforming anchor with an opening through which the external ear may be passed. The ear protector further comprises an insulating outer covering that, in combination with the anchor, forms the ear protector with a chamber positioned between the outer covering and the anchor. During use, the chamber is configured to receive the external ear, with the anchor's opening conformably positioned in proximity to at least a portion of the ear's root. The perimeter of the conforming anchor's opening resiliently deforms during passage of the external ear through the opening and into the chamber, and then conforms to the geometry of at least a portion of the ear root in order to securely and comfortably maintain the ear protector in position over the external ear without additional external support. The conforming anchor preferably is fabricated from a closed cell foamed elastomer.

18 Claims, 21 Drawing Sheets

(56) References Cited

U.S. PATENT DOCUMENTS

| | | |
|---|---|---|
| 3,452,365 A | 7/1969 | Wallace |
| 3,525,103 A | 8/1970 | Yonan |
| 3,823,713 A * | 7/1974 | Shah .......................... 602/74 |
| D267,286 S | 12/1982 | Anderie |
| 4,660,229 A | 4/1987 | Harris |
| 4,670,911 A * | 6/1987 | Dunford ...................... 2/209 |
| 4,682,374 A | 7/1987 | Geiser |
| 4,713,843 A | 12/1987 | Duncan |
| 4,791,684 A | 12/1988 | Schwartz |
| 4,872,219 A | 10/1989 | Duncan |
| 4,935,965 A | 6/1990 | Wassell |
| 5,086,789 A | 2/1992 | Tichy |
| D328,160 S | 7/1992 | Sudduth |
| D344,611 S | 2/1994 | Hordis |
| 5,339,467 A | 8/1994 | Brinkley |
| 5,477,564 A | 12/1995 | Tichy |
| D374,508 S | 10/1996 | Walker-Whitelaw |
| 5,615,417 A | 4/1997 | Jackson |
| 5,778,455 A | 7/1998 | Joseph |
| 5,898,945 A | 5/1999 | Weiser |
| 5,920,912 A | 7/1999 | Patchett |
| 6,055,672 A | 5/2000 | Natvig |
| 6,154,890 A * | 12/2000 | Deopuria et al. ............ 2/423 |
| 6,298,493 B1 | 10/2001 | Ambroise |
| 6,392,196 B1 * | 5/2002 | Lin ............................ 219/211 |
| 6,880,174 B2 | 4/2005 | Prokop |
| 6,976,275 B1 | 12/2005 | Liu |
| 7,006,649 B2 | 2/2006 | Natvig |
| 7,028,343 B1 * | 4/2006 | Watson ............... A45D 44/12 2/174 |
| 7,212,645 B2 | 5/2007 | Le Gette et al. |
| D547,008 S | 7/2007 | Machold |
| 7,469,429 B1 | 12/2008 | Lanclos |
| 7,614,089 B2 | 11/2009 | Hillman-Schwartz et al. |
| 2009/0178177 A1 * | 7/2009 | Fairclough et al. ............ 2/209 |

\* cited by examiner

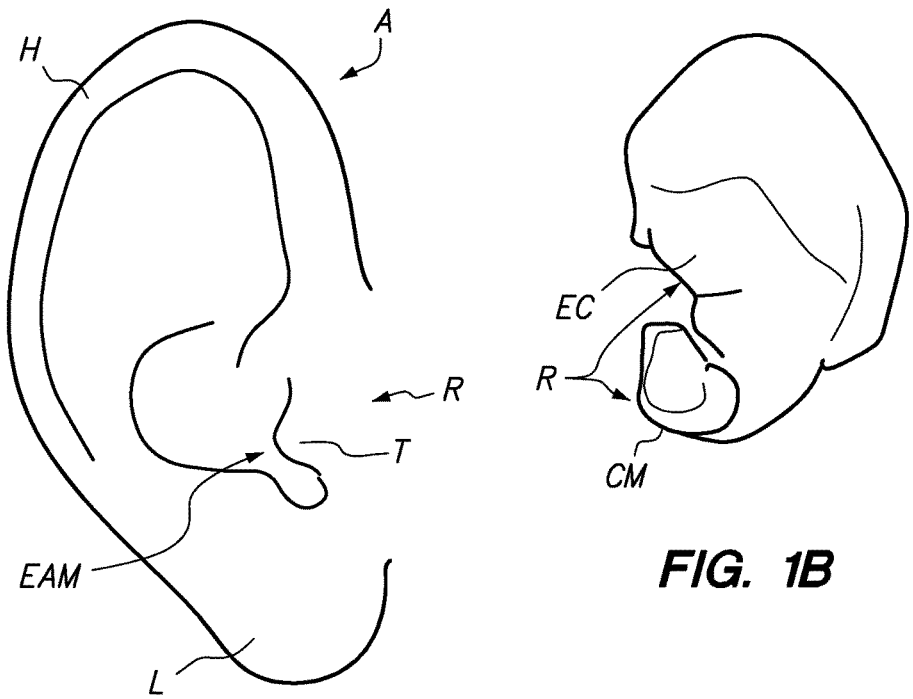
FIG. 1A
FIG. 1B
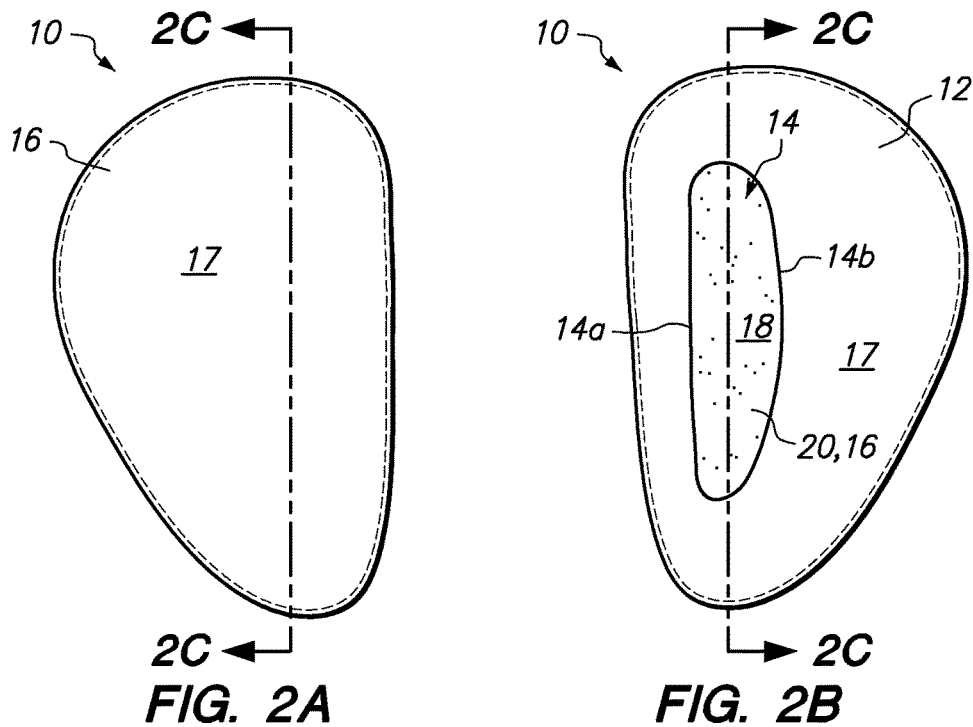
FIG. 2A
FIG. 2B

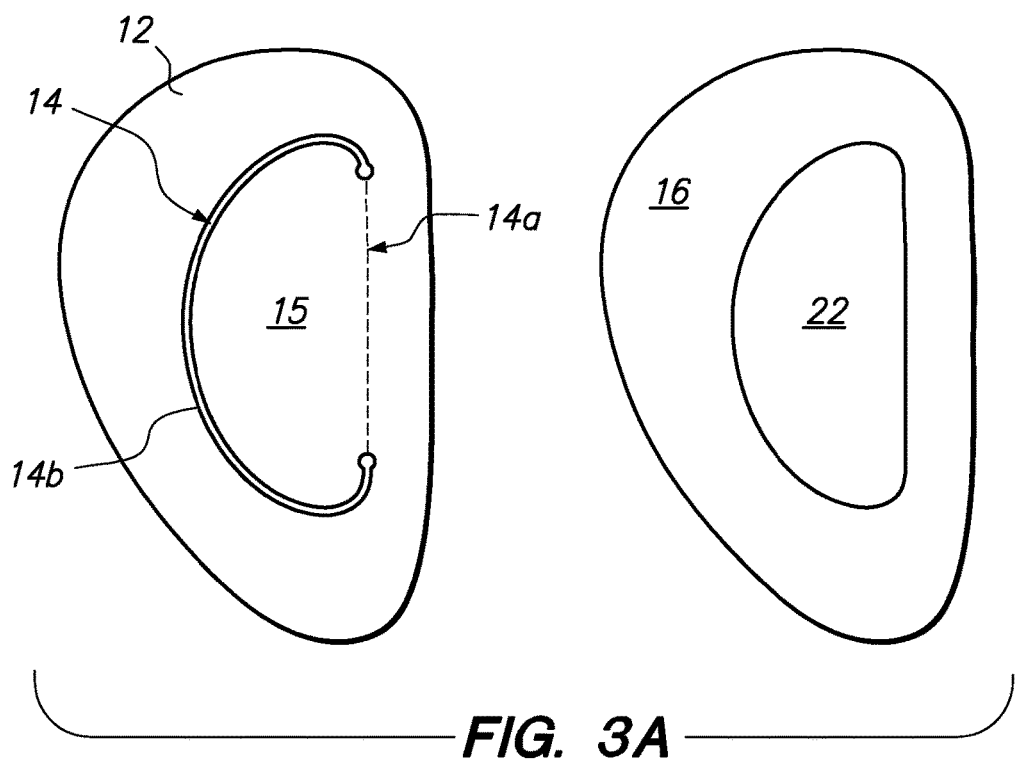
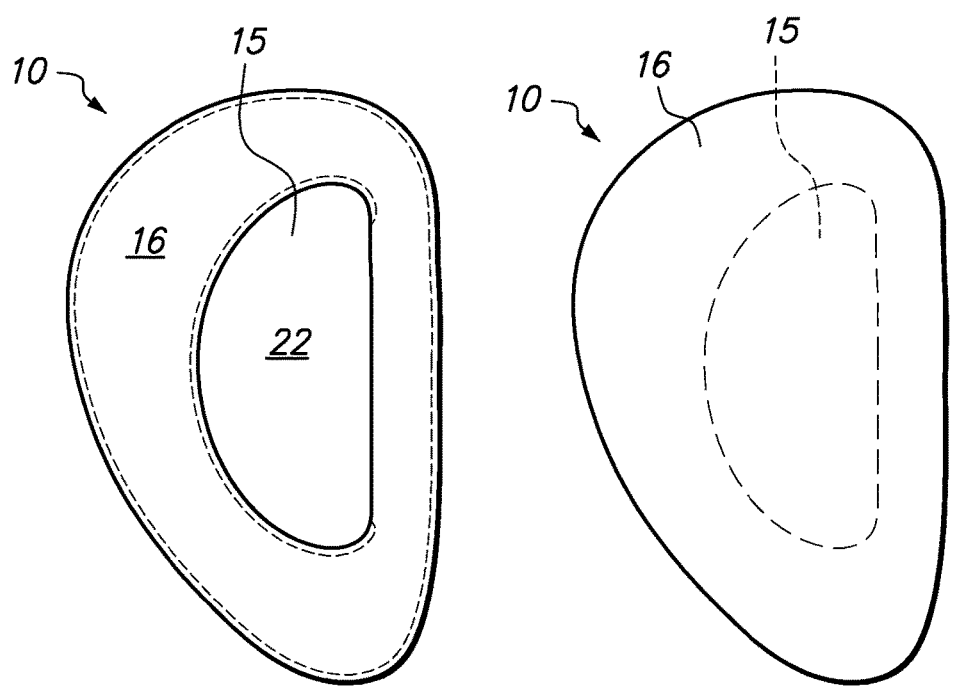
FIG. 3A
FIG. 3B          FIG. 4

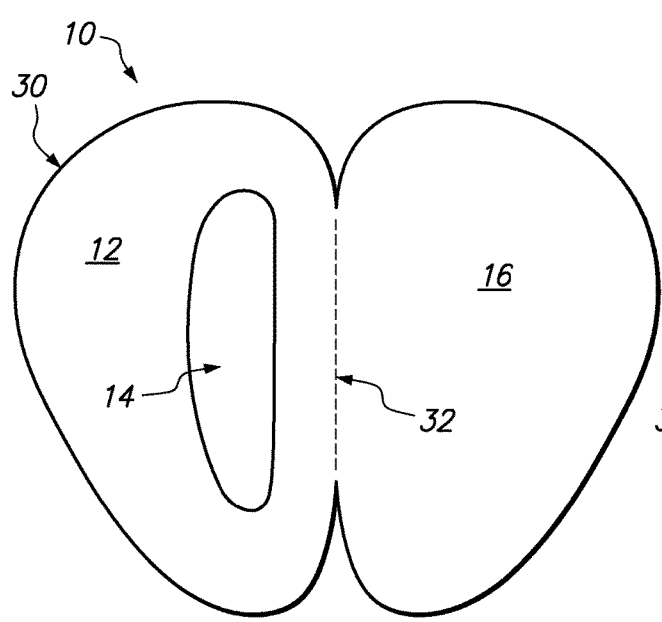
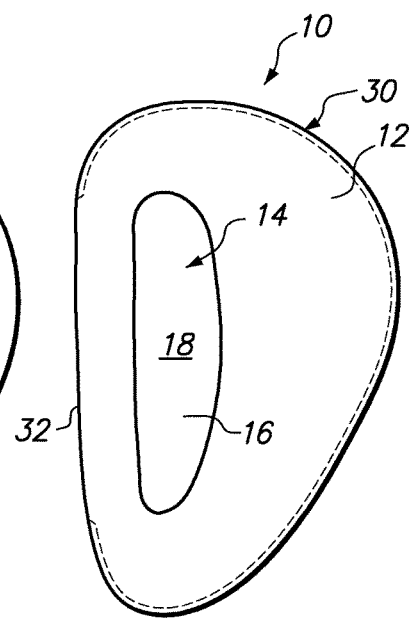
FIG. 5A        FIG. 5B
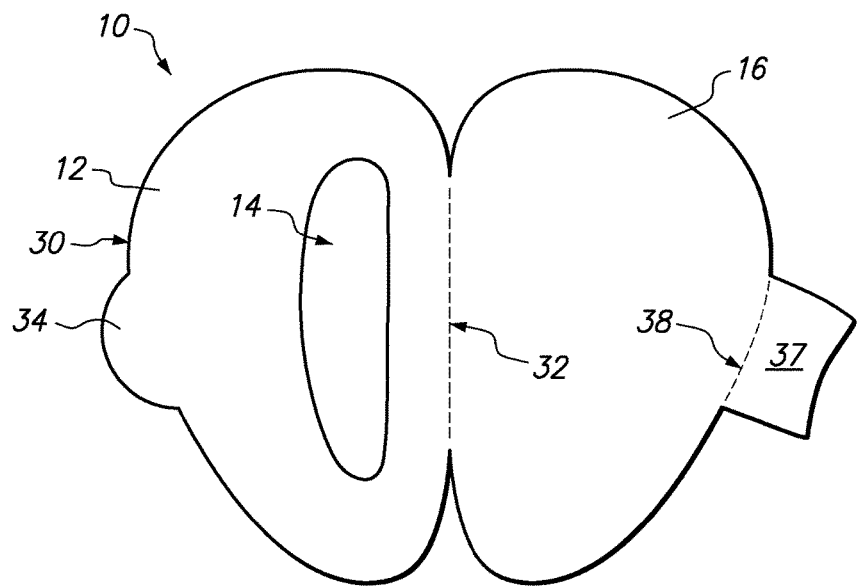
FIG. 6A

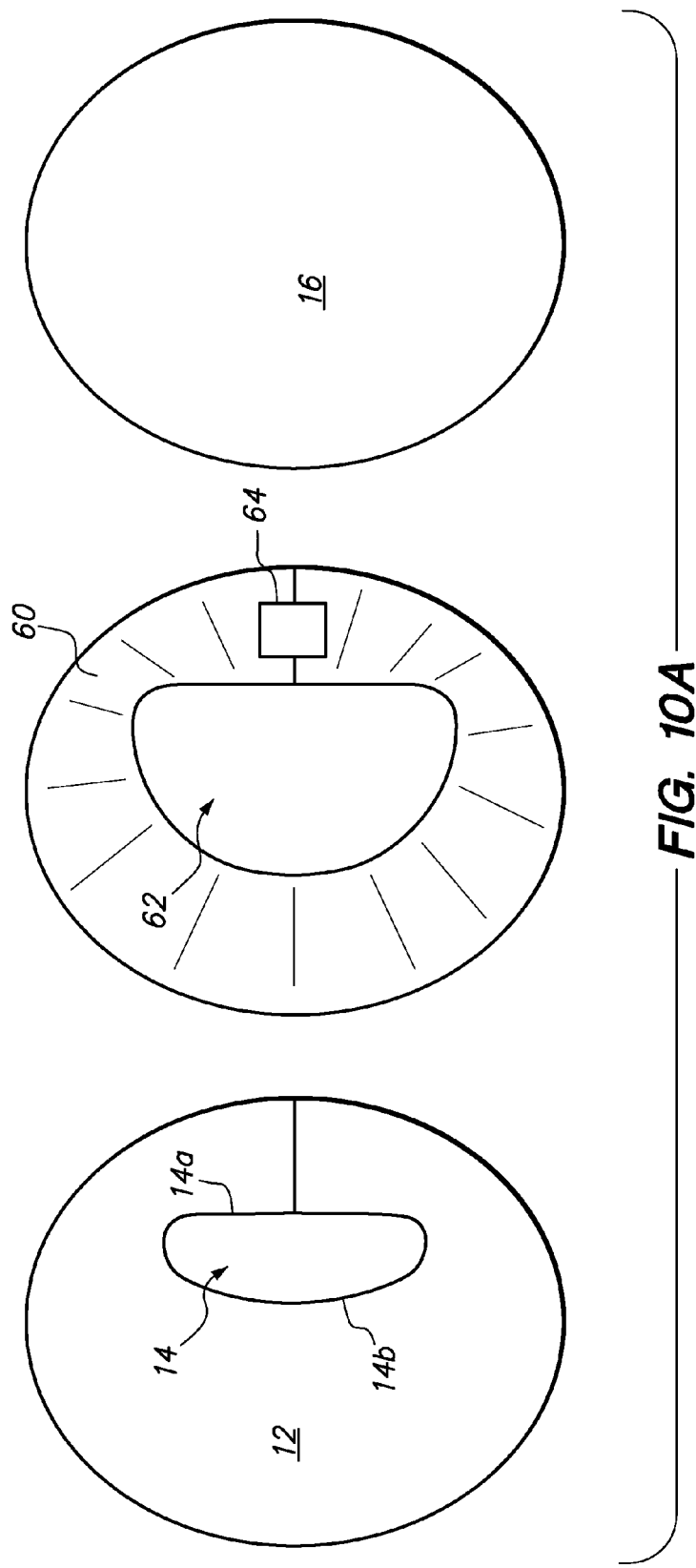

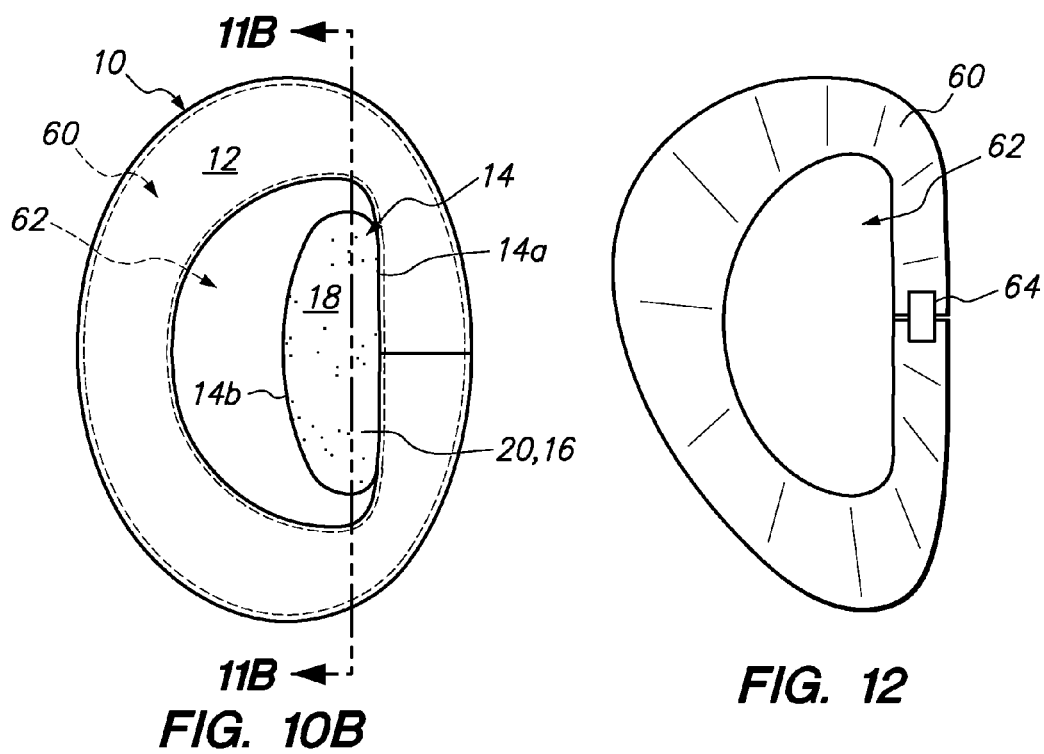
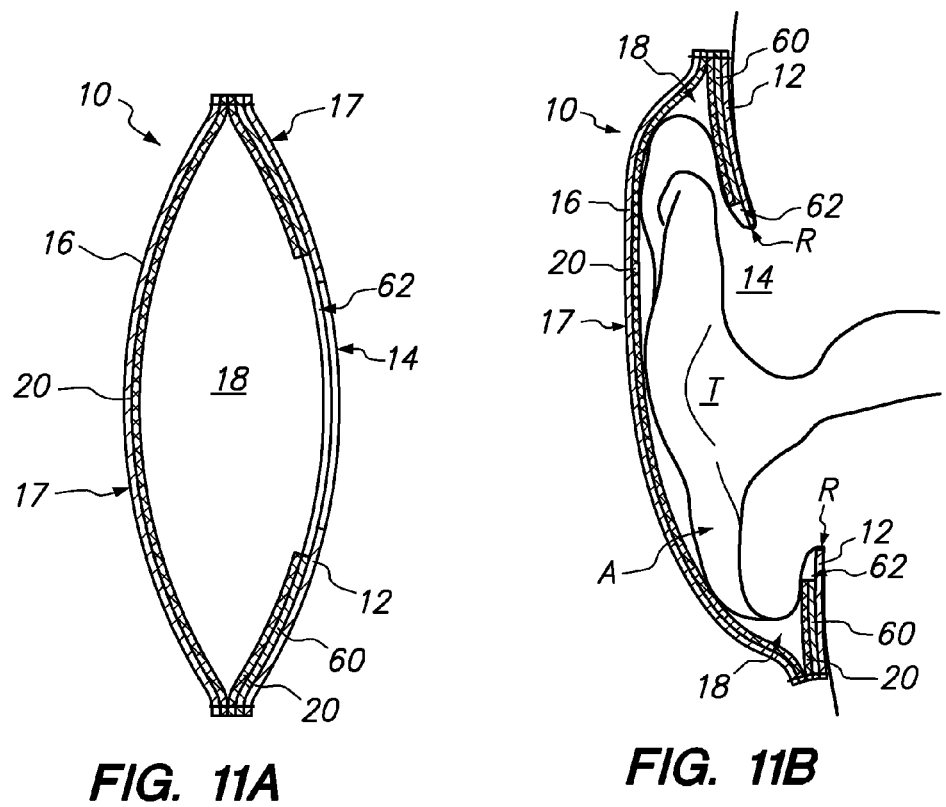
FIG. 10B
FIG. 12
FIG. 11A
FIG. 11B

METHODS AND APPARATUS FOR EAR PROTECTION

REFERENCE TO RELATED APPLICATIONS

The present application claims priority and the benefit of the filing dates of U.S. provisional patent application Ser. No. 61/417,161, filed Nov. 24, 2010, and U.S. provisional patent application Ser. No. 61/434,359, filed Jan. 19, 2011, both of which are incorporated herein by reference in their entireties.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present invention relates to methods and apparatus for ear protection. More particularly, the present invention relates to methods and apparatus for protecting the ear from the elements, e.g., heat, cold, wind, rain, snow and/or other elements, via an ear protector. In some embodiments, the ear protector comprises a conforming anchor with an opening through which the external ear may be passed. The ear protector further comprises an insulating outer covering that, in combination with the anchor, forms the ear protector with a chamber or space positioned between the outer covering and the anchor. During use, the chamber is configured to receive the external ear, with the anchor's opening conformably positioned in proximity to at least part of the ear's root. The perimeter of the conforming anchor's opening (which generally has a smaller maximum linear dimension than a maximum linear dimension of the external ear) is configured to resiliently deform during passage of the external ear through the opening and into the chamber, and then to conform to the geometry of at least part of the ear root in order to securely and comfortably maintain the ear protector in position over the external ear without additional external support.

BACKGROUND

Various methods and apparatus have been devised for protecting the ears from the elements, heat, cold and/or wind. As an alternative to hats or hoods that cover both the head and the ears, earmuffs are often used when a protective covering is desired for the ears, but not for the head. Earmuffs also may be used in combination with hats or hoods when additional protection is desired for the ears. However, earmuffs generally require a band that is placed over the top of the head, or around the back of the head and/or neck, to connect the two earmuffs and keep them in place over the ears (see, for example, U.S. Pat. No. 6,880,174 to Prokop, which is incorporated herein by reference in its entirety).

Bandless earmuffs (i.e., earmuffs without a band over the top, or around the back, of the head/neck), or ear protectors, have been devised that engage the ear directly for maintenance without additional external support. These bandless earmuffs often comprise one of two basic designs: a bistable, truncated cone for reversibly clamping the ear, or an elastic band that may be stretched for placement over the ear.

Bistable truncated cone designs are described, for example, in U.S. Pat. Nos. 2,325,150 to Sahlmann; 2,378,398 to Fiedler; 3,112,493 to Greenberg; 4,713,843 and 4,872,219 to Duncan; 5,339,467 to Brinkley; 5,898,945 to Weiser; and 6,055,672 and 7,006,649 to Natvig, all of which are incorporated herein by reference in their entireties. Elastic band designs are described, for example, in U.S. Pat. No. 5,778,455 to Joseph, and U.S. Pat. No. 6,298,493 to Ambroise, both of which are incorporated herein by reference.

With reference to the bistable truncated cone designs, the bandless earmuffs generally comprise an annular segment of a rigid or semi-rigid material, such as plastic cut from a sheet, that is formed into a bistable truncated cone, e.g., by cutting the annular segment to create two edges (e.g., creating a "C"-shaped segment) that are approximated and/or overlapped and secured, or by thermoforming the annular segment into the truncated cone shape. Alternatively, the bistable truncated cone may be formed directly via injection molding. The truncated cone is bistable, such that it may be everted from a concave to a convex configuration.

While in the convex configuration, the truncated cone is configured for passage over an external ear, such that the cone may be placed against a cranial (i.e., back or inner) surface of the ear without substantially deforming the truncated cone. An outer covering is coupled to the bistable truncated cone for covering a lateral (i.e., front or outer) surface of the external ear, thereby forming a bandless earmuff. While the cone is in its stable convex configuration, a chamber or space is formed between the outer covering and the bistable truncated cone, which facilitates passage of the external ear through the opening in the truncated cone into the chamber. After placement of the ear within the chamber, the truncated cone may be flexed to evert the cone to its stable concave configuration, thereby clamping the ear between the cone and the outer covering and securing the bandless earmuff to the ear without additional external support.

With reference to the elastic band designs, a pouch of flexible material is formed for placement over the ear. All or a portion of the opening of the pouch may be attached to an elastic band and/or may be wrapped around the elastic band and secured, e.g., sewn or glued, to itself, such that the elastic band is positioned within a pocket about all or a portion of the perimeter of the pouch's opening. When the elastic band is formed into a loop with its ends attached to one another, the elastic band may, or may not, be attached to the flexible material of the pouch, e.g., at or near its attached ends. When the elastic band is not formed into a loop, the elastic band may be attached to the flexible material at least at or near its ends.

In an unstressed configuration, the elastic band generally has a linear length that is less than the unstressed linear length of the pouch opening (or the portion of the pouch opening that it circumscribes). As such, the flexible material of the pouch generally is bunched locally to provide additional material to facilitate elastic deformation of the elastic band to reversibly enlarge the opening of the pouch for placement of the ear within the pouch. After placement of the ear within the pouch, the elastic band shortens, which reduces the size of the pouch opening and engages the ear to maintain the pouch over the ear.

While both bistable truncated cone designs and elastic band designs reversibly engage the ear and may be utilized to secure bandless earmuffs to the ear, each has drawbacks. In the secured concave configuration of the bistable truncated cone designs, the ear may be clamped between the cone and the outer covering with substantial force to ensure that the cone is maintained in the concave configuration and to form a secure clamp. While effective, this clamping mechanism may be uncomfortable since the ear is continuously squeezed, often for an extended period of time. Furthermore, since the opening in the truncated cone is of generally fixed perimeter geometry and size, the cone may not be configured for passage over a large range of ear sizes and/or the relatively rigid edge of the truncated cone's opening may uncomfortably abut the ear root. Alternatively, the truncated cone may clamp the ear at or near its helix, leaving a portion of the ear unprotected along its cranial surface between the ear root and the edge of the truncated cone and enhancing a risk of the ear protector sliding off the ear due to instability and insufficient clamping.

In the elastic band designs, the localized bunching and additional pouch material necessary to facilitate expansion of the pouch opening for placement of the pouch around the ear may provide a profile during use that is unsightly, unfashionable and/or is not streamlined. Furthermore, the elastic band and/or the bunched pouch material may uncomfortably impinge on the ear root and/or may apply stress to the ear root non-uniformly with uncomfortable areas of stress concentration. Furtherstill, the localized bunching of the pouch material and/or the limited elasticity of the elastic band may preclude use of some pouch materials possessing desirable thermal characteristics, for example, due to the thickness and/or relative resilience of such materials.

In view of the foregoing, it would be desirable to provide methods and apparatus for ear protection that overcome the drawbacks of previously known methods and apparatus.

SUMMARY

The present invention relates to methods and apparatus for ear protection. More particularly, the present invention relates to methods and apparatus for protecting the ear from the elements, heat, cold and/or wind via an ear protector. In some embodiments, the ear protector comprises a conforming anchor with an opening through which the external ear may be passed. The anchor and/or its opening may, for example, be generally annular "O"- or "D"-shaped, "C"-shaped, kidney-shaped, auricula-shaped, or ear root-shaped for placement of the opening around the ear root. The ear protector further comprises an insulating outer covering that, in combination with the anchor, forms the ear protector with a chamber or space positioned between the outer covering and the anchor.

During use, the chamber is configured to receive the external ear, with the anchor's opening conformably positioned in proximity to at least a portion of the ear's root. A perimeter of the conforming anchor's opening (which generally has a smaller maximum linear dimension than a maximum linear dimension of the external ear) is configured to resiliently deform during passage of the external ear through the opening and into the chamber, and then to conform to the geometry of at least a portion of the ear root in order to securely and comfortably maintain the ear protector in position over the external ear without additional external support.

The conforming anchor preferably is fabricated from an elastomer, such as a foamed elastomer. The elastomer utilized to fabricate the conforming anchor preferably comprises a closed cell foam. Elastomers generally are vulcanized thermosets, but also may be thermoplastics. Elastomers generally are viscoelastic with relatively low Young's modulus and high yield strain. In addition to their high capacity for elastic deformation, some foamed elastomers may possess highly desirable insulating thermal properties, such as very low thermal conductivity. As such, the ear protector's outer covering optionally also may be fabricated from one or more foamed elastomers, e.g., the outer covering may be fabricated from the same elastomer(s) used to fabricate the conforming anchor.

Examples of thermoset and thermoplastic elastomers include, for example, natural rubber (polyisoprene), synthetic polyisoprene, butyl rubber, polybutadiene, styrene-butadiene rubber, nitrile rubber, chloroprene rubber, polychloroprene (e.g., Neoprene marketed by DuPont of Wilmington, Del.), ethylene propylene rubber, ethylene propylene diene rubber, epichlorohydrin rubber, polyacrylic rubber, silicone rubber, fluorosilicone rubber, fluoroelastomers, perfluoroelastomers, polyether block amides, chlorosulfonated polyethylene, ethylene-vinyl acetate, styrenic block copolymers, polyolefin blends, elastomeric alloys, thermoplastic polyurethanes, thermoplastic copolyester, thermoplastic polyamides, thermoplastic vulcanizates, polysulfide rubber, etc. The conforming anchor (and, optionally, the outer covering) may comprise one or more of these—or other—elastomers, as desired. In one variation, the conforming elastomer anchor comprises polyisoprene. In another variation, the conforming elastomer anchor comprises styrene-butadiene rubber. In yet another variation, the conforming elastomer anchor comprises polychloroprene, e.g., Neoprene.

Optionally, foamed elastomer(s) utilized to fabricate the anchor and/or the outer covering may be backed on one or both outer surfaces with a backing material, such as a nylon or spandex fabric sheet, and/or a loop material configured to engage a mating hook material (or vice versa). Backing materials may reduce a risk of sticking between the foamed elastomer and the surface of the skin. They also may significantly reduce the likelihood of plastic deformation and failure (e.g., tearing or ripping) of the foamed elastomer during use.

In contrast to known ear protectors with bistable truncated cone designs, in some embodiments the conforming anchor of the present invention's ear protector does not evert in order to anchor the ear protector to the ear, which may simplify use dynamics. Furthermore, in some embodiments the present invention's ear protector does not clamp the ear between the outer covering and the anchor, which may increase comfort. Additionally, the opening in the anchor of the present invention's ear protector is resiliently deformable and thus does not comprise a generally fixed perimeter geometry and size, thereby facilitating passage of the anchor over a large range of ear/ear root sizes. Also, since the opening in the anchor of the present invention's ear protector is pliant rather than relatively rigid, at least a portion of an edge of the opening comfortably conforms to at least a portion of the contours of the ear root.

In contrast to known ear protectors with elastic band designs, the conforming anchor of the present invention's ear protector does not required localized bunching and additional anchor material in order to facilitate resilient expansion of the anchor's opening for placement of the anchor around the ear, thereby facilitating fabrication of an ear protector that more closely follows the profile of the ear, e.g., that is more attractive, fashionable and/or streamlined. Furthermore, the profile of the opening in the anchor of the present invention's ear protector may be configured such that it conforms to the ear root without uncomfortably impinging on the ear root, e.g., such that stress is applied to the ear root in a relatively uniform fashion without uncomfortable areas of stress concentration. Furtherstill, the present invention's ear protector anchor and/or outer covering may be fabricated from foamed elastomers possessing desirable thermal properties; such foamed elastomers may be too thick and/or resilient for use with known elastic band designs.

Although in some embodiments the conforming anchor of the present invention's ear protector possesses neither a bistable truncated cone for clamping to the ear nor an elastic band for engaging the ear, it should be understood that such cones and/or elastic bands optionally may be provided in combination with the conforming anchor of the present invention's ear protector.

Ear protectors of the present invention optionally may comprise one or more communication elements and/or active thermal elements. Furthermore, ear protectors of the present invention may comprise a flap configured to extend forward (anterior) from the ear to the block the elements from the external ear and the ear canal.

BRIEF DESCRIPTION OF THE DRAWINGS

Several embodiments of the present invention will be apparent upon consideration of the following detailed description, taken in conjunction with the accompanying drawings, in which like reference characters refer to like parts throughout, and in which:

FIGS. 1A and 1B are schematic views of the lateral and cranial surfaces, respectively, of the human external ear;

FIGS. 2A-2C are, respectively, schematic views of the lateral and cranial surfaces of an ear protector in accordance with the present invention, and a sectional view of the ear protector along the section line 2C of FIGS. 2A and 2B, illustrating a method of use;

FIGS. 3A and 3B are, respectively, schematic views of a partially assembled and fully assembled embodiment of the ear protector of FIG. 2 comprising a flap of material;

FIG. 4 is a schematic view of a variation of the ear protector embodiment of FIG. 3;

FIGS. 5A and 5B are, respectively, schematic views of a partially assembled and fully assembled embodiment of the ear protector of FIG. 2 comprising a unitary anchor and outer covering;

FIGS. 6A and 6B are, respectively, schematic views of a partially assembled and fully assembled embodiment of the ear protector of FIG. 2 comprising ear protector placement/removal facilitators;

FIGS. 10A and 10B are, respectively, schematic views of a partially assembled and fully assembled embodiment of the ear protector of FIG. 2 comprising a conforming anchor in combination with a bistable truncated cone ear clamp;

FIGS. 11A and 11B are schematic sectional views of the ear protector of FIG. 10 along section line 11B of FIG. 10B, illustrating a method of using the ear protector and showing, respectively, placement of the ear clamp in a convex configuration for receipt and/or removal of the ear from within the ear protector, and in a concave configuration for clamping the ear between the ear clamp and the outer covering while the conforming anchor engages at least a portion of the ear root;

FIG. 12 is a schematic view of a bistable truncated cone ear clamp for use with a variation of the ear protector of FIGS. 10 and 11 exhibiting minor axis asymmetry;

DETAILED DESCRIPTION

Figure 2C:
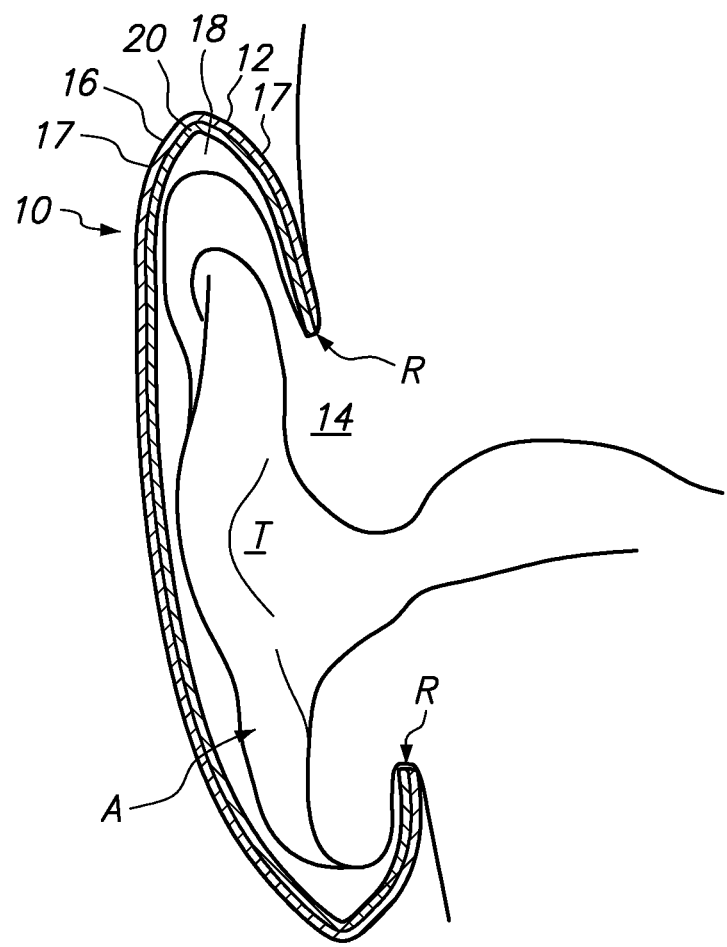

Although the disclosure hereof is detailed and exact to enable those skilled in the art to practice the disclosed technologies, the physical embodiments herein disclosed merely exemplify the various aspects of the invention, which may be embodied in other specific structures. While the preferred embodiments are described, the details may be changed without departing from the invention, which is defined by the claims.

I. Pertinent Anatomy

With reference to FIGS. 1A and 1B, pertinent anatomy of the external ear is described. The external ear consists of a pinna or auricula A that projects from the side of the head, and an external acoustic meatus EAM that leads inward to the tympanic cavity. As seen in FIG. 1A, the outer perimeter of the lateral (i.e., front or outer) surface of the external ear is defined by the helix H, lobule L and tragus T. As seen in FIG. 1B, the inner perimeter of the cranial (i.e., back or inner) surface of the external ear is defined by its connection to the cranium along the origins of the cartilage of meatus CM and the eminentia conchae EC. For the purposes of the present invention, ear root R is defined as the perimeter where the auricula A attaches to the cranium, e.g., the perimeter defined by the origins of the cartilage of meatus CM and eminentia conchae EC along the ear's cranial surface, and by the origin of the tragus T along the ear's lateral surface. Ear protectors in accordance with the present invention may conformably engage all or part of the ear root while covering all or part of the auricula.

II. Methods and Apparatus for Ear Protection

A. Overview

The present invention relates to methods and apparatus for ear protection. More particularly, the present invention relates to methods and apparatus for protecting the ear from heat, cold, rain, snow, wind and/or other elements via an ear protector. As seen in FIGS. 2A and 2B, ear protector 10 comprises a conforming anchor 12 with opening 14 through which the external ear may be passed. The anchor opening may, for example, be generally annular "O"- or "D"-shaped, "C"-shaped, kidney-shaped, auricula-shaped, or ear root-shaped for placement of the opening around the ear root R. Opening 14 may, for example, comprise a maximum dimension along its major axis (i.e., the axis that generally extends vertically when the ear protector is positioned over the ear of a standing person) in the range of about 1 inch to 2.5 inches (e.g., in the range of about 2.5 cm to 6.5 cm). More preferably, the opening may comprise a maximum dimension along its major axis in the range of about 1.5 inches to 2 inches (e.g., in the range of about 3.75 cm to 5 cm). Furthermore, opening 14 may, for example, comprise a maximum dimension along its minor axis (i.e., the axis that generally extends vertically when the ear protector is positioned over the ear of a standing person) in the range of about zero inches (i.e., a slit) to 1 inch (e.g., in the range of about zero cm to 2.5 cm). More preferably, the opening may comprise a maximum dimension along its minor axis in the range of about 0.25 inches to 0.75 inches (e.g., in the range of about 0.5 cm to 2 cm).

The ear protector 10 further comprises an insulating outer covering 16 that, in combination with the anchor 12, forms the ear protector with a chamber or space 18 positioned between the outer covering 16 and the anchor 12. The anchor 12 and outer covering 16 may be formed from separate pieces of material that are joined (e.g., sewn, glued, bonded, hook-and-loop fastened or 'Velcroed', or otherwise attached)—either permanently or reversibly—at or near their outer perimeters, and/or the anchor and outer material may be formed from a single piece of material that is folded over upon itself and secured (e.g., sewn, glued, bonded, hook-and-loop fastened, etc.)—either permanently or reversibly—at or near the outer perimeter of the folded single piece. Optionally, ear protector 10 may be everted upon itself prior to use in order to provide the ear protector with an unstressed profile that maintains chamber 18 in a relatively open configuration for receiving the external ear.

Ear protector 10 may, for example, comprise a maximum dimension along its major axis (i.e., the axis that generally extends superior-inferior or vertically when the ear protector is positioned over the ear of a standing person) in the range of about 2 inches to 4.5 inches (e.g., in the range of about 5 cm to 11.5 cm). More preferably, the ear protector may comprise a maximum dimension along its major axis in the range of about 2.5 inches to 4 inches (e.g., in the range of about 6.5 cm to 10 cm). Furthermore, ear protector 10 may, for example, comprise a maximum dimension along its minor axis (i.e., the axis that generally extends anterior-posterior or horizontally when the ear protector is positioned over the ear of a standing person) in the range of about 1.5 inches to 3 inches (e.g., in the range of about 4 cm to 8 cm). More preferably, the ear protector may comprise a maximum dimension along its minor axis in the range of about 1.5 inches to 2.5 inches (e.g., in the range of about 4 cm to 7 cm).

Note that these exemplary minor axis maximum dimensions for the ear protector relate to a fully formed ear protector while in use. Thus, for example, when the anchor and outer covering of the ear protector are fabricated from a single piece, the ear protector's minor axis maximum dimension would relate to the maximum dimension after folding over and securing of the single piece upon itself, not the maximum dimension prior to such folding/securing. Multiple sizes of ear protector 10 may be provided to accommodate different ear geometries.

As seen in FIG. 2C, chamber 18 of ear protector 10 is configured to receive the external ear auricula A, with at least a portion of an edge of the anchor's opening 14 conformably positioned in proximity to all or a portion of the ear's root. The perimeter of the conforming anchor's opening 14 (which generally has a smaller maximum linear dimension than a maximum linear dimension of the external ear auricula A) is resiliently deformed during passage of the auricula A through opening 14 and into chamber 18, and the opening spontaneously conforms to the geometry of the ear root R in order to securely and comfortably maintain the ear protector 10 in position over the external ear auricula without additional external support. The edge of opening 14 comprises a lateral portion 14a configured for placement in proximity to the ear root R along the lateral surface of the ear (e.g., along the origin of tragus T), as well as a cranial portion 14b configured for placement in proximity to the ear root R along the cranial surface of the ear (e.g., along the origins of the cartilage of meatus CM and eminentia conchae EC).

As also seen in FIG. 2C, one or more additional layers of material 20 may be attached to the anchor 12 and/or to the outer covering 16, e.g., to enhance insulation of chamber 18 from ambient conditions, to provide a desired texture at the interface between the ear protector 10 and the wearer's ear within chamber 18, to enhance weather protection/waterproofing, etc. Material layer(s) 20 may be attached to any surface of ear protector 10, as desired, and preferably are attached to the surface(s) disposed within chamber 18. Exemplary material layers 20 include, for example, fleece, wool, insulation (e.g., Thinsulate® marketed by 3M Corporation of St. Paul, Minn.), fabric protectors, polytetrafluoroethylene (e.g., Teflon® marketed by DuPont of Wilmington, Del.), denim, fur, leather, suede, velvet, faux fur, faux leather (e.g., vinyl), faux suede, combinations thereof, etc.

The conforming anchor 12 preferably is fabricated from an elastomer, such as a foamed elastomer. The elastomer utilized to fabricate the anchor preferably comprises a closed cell foam. The foamed elastomer preferably comprises a thickness in the range of about 0.02"-0.40" (e.g., in the range of about 0.5 mm-1 cm), more preferably a thickness in the range of about 0.04"-0.20" (e.g., in the range of about 1 mm-5 mm), even more preferably a thickness in the range of about 0.06"-0.12" (e.g., a thickness in the range of about 1.5 mm-3 mm).

Elastomers generally are vulcanized thermosets, but also may be thermoplastics. Elastomers generally are viscoelastic with relatively low Young's modulus and high yield strain. In addition to their high capacity for elastic deformation, some foamed elastomers may possess highly desirable insulating thermal properties, such as very low thermal conductivity. As such, the ear protector's outer covering 16 optionally also may be fabricated from one or more foamed elastomers, e.g., the outer covering 16 may be fabricated from the same elastomer(s) used to fabricate the conforming anchor 12.

Examples of thermoset and thermoplastic elastomers include, for example, natural rubber (polyisoprene), synthetic polyisoprene, butyl rubber, polybutadiene, styrene-butadiene rubber, nitrile rubber, chloroprene rubber, polychloroprene (e.g., Neoprene marketed by DuPont of Wilmington, Del.), ethylene propylene rubber, ethylene propylene diene rubber, epichlorohydrin rubber, polyacrylic rubber, silicone rubber, fluorosilicone rubber, fluoroelastomers, perfluoroelastomers, polyether block amides, chlorosulfonated polyethylene, ethylene-vinyl acetate, styrenic block copolymers, polyolefin blends, elastomeric alloys, thermoplastic polyurethanes, thermoplastic copolyester, thermoplastic polyamides, thermoplastic vulcanizates, polysulfide rubber, etc. The conforming anchor 12 (and, optionally, the insulating outer covering 16) may comprise one or more of these—or other—foamed elastomers, as desired. In one variation, the conforming foamed elastomer anchor 12 comprises polyisoprene. In another variation, the conforming foamed elastomer anchor 12 comprises styrene-butadiene rubber. In yet another variation, the conforming foamed elastomer anchor 12 comprises polychloroprene, e.g., Neoprene.

Optionally, foamed elastomer(s) utilized to fabricate anchor 12 and/or outer covering 16 may be backed on one or both surfaces (i.e., one or both of the interior outer surface and the exterior outer surface) with a backing material 17, such as a nylon or spandex fabric sheet, and/or a loop material configured to engage a mating hook material (or vice versa). Backing materials 17 may reduce a risk of sticking between the foamed elastomer and the surface of the skin. They also may significantly reduce the likelihood of plastic deformation and failure (e.g., tearing or ripping) of the foamed elastomer during use. Furthermore, they may comprise a component of a reversible fastener, such as the loop component of a hook-and-loop-type fastener, as described in more detail herein below.

In contrast to known ear protectors with bistable truncated cone designs, in some embodiments the conforming anchor 12 of the present invention's ear protector 10 does not evert in order to anchor the ear protector 10 to the ear, which may simplify use dynamics. Furthermore, in some embodiments the present invention's ear protector 10 does not clamp the ear between the outer covering 16 and the anchor 12, which may increase comfort. Additionally, the opening 14 in the anchor 12 of the present invention's ear protector 10 is resiliently deformable and thus does not comprise a generally fixed perimeter geometry and size, thereby facilitating passage of the anchor 12 over a large range of ear/ear root sizes. Also, since the opening 14 in the anchor 12 of the present invention's ear protector 10 is pliant rather than relatively rigid, at least a portion of the edge of the opening 14 comfortably conforms to at least a portion of the contours of the ear root R.

In contrast to known ear protectors 10 with elastic band designs, the conforming anchor 12 of the present invention's ear protector 10 does not require localized bunching and additional anchor material in order to facilitate expansion of the anchor's opening 14 for placement of the anchor 12 around the ear, thereby facilitating fabrication of an ear protector 10 that more closely follows the profile of the ear, e.g., that is more attractive, fashionable and/or streamlined. Furthermore, the profile of the opening 14 in the anchor 12 of the present invention's ear protector may be configured such that it conforms to the ear root R without uncomfortably impinging on the ear root, e.g., such that stress is applied to the ear root R in a relatively uniform fashion without uncomfortable areas of stress concentration. Furtherstill, the present invention's ear protector anchor and/or outer covering may be fabricated from foamed elastomers possessing desirable thermal properties; such foamed elastomers may be too thick and/or resilient for use with known elastic band designs.

Although, in the illustrative embodiment of FIG. 2, the conforming anchor 12 of the present invention's ear protector 10 is provided with neither a bistable truncated cone for clamping to the ear nor an elastic band for engaging the ear, it should be understood that such cones and/or elastic bands optionally may be provided in combination with the conforming anchor 12 of the present invention's ear protector 10.

B. Specific Embodiments

1. Flap

The anchor 12 and its opening 14 may, for example, be mechanically-, thermally-, fluidically-, water jet-, laser-, die- and/or otherwise cut or stamped from a sheet of foamed elastomer. Optionally, outer covering 16 also may be cut or stamped from a sheet of foamed elastomer. Optionally, the anchor 12 and the outer covering 16 may be formed from a single piece of foamed elastomer that is folded over upon itself, then secured along its edge to form ear protector 10 with chamber 18 (see, e.g., FIG. 5).

As seen in FIG. 3A, ear protector 10 may be fabricated from a conforming anchor 12 having an opening 14 that comprises a flap 15 of the foamed elastomer. The flap is connected to anchor 12 along lateral portion 14a of the opening 14, but is detached along cranial portion 14b. In some embodiments (see, e.g., FIGS. 24-25), the flap 15 may be folded back towards or upon the anchor 12 in the vicinity of lateral portion 14a during use, such that the opening is unobstructed and the flap lies against the wearer's head, extending or projecting towards the anterior of the wearer's head (i.e., extending towards the wearer's face). In this manner, the flap 15 may at least partially block cold, heat, wind, rain and/or other elements from the wearer's external ear and/or ear canal, while also facilitating placement/removal of the ear protector 10 by providing an element that may be grasped during such placement/removal. In other embodiments, such as the embodiment of FIG. 3, the flap 15 optionally may be configured to at least partially cover the lateral surface of the auricula A during use, with at least a portion of the edge of opening 14 conformably engaging at least a portion of the ear root R.

As also seen in FIG. 3A, outer covering 16 optionally may comprise a flapless opening 22 that corresponds to the geometry of flap 15. As seen in FIG. 3B, anchor 12 may be permanently or reversibly attached to outer covering 16 (e.g., via sewing, gluing, bonding, hook-and-loop fastening or 'Velcroing', or any other technique) at or near all or a portion of its outer perimeter, while all or a portion of the outer perimeter of flap 15 optionally may be attached to all or a portion of the edge of flapless opening 22 (optionally, flap 15 may be attached or left unattached to flapless opening 22 of outer covering 16 along lateral portion 14a of opening 14 of anchor 12). This forms ear protector 10 with chamber 18 for fully enclosing the auricula A. As previously discussed, the ear protector optionally may be everted prior to use in order to provide ear protector 10 with an unstressed profile that maintains chamber 18 in a relatively open configuration.

In use, flap 15 and outer covering 16 may envelop the lateral surface of the auricula A, while anchor 12 may envelop the cranial surface with opening 14 at least partially engaging ear root R. Opening 14 is configured to resiliently deform during passage of the auricula into chamber 18, then to at least partially conform to ear root R.

Referring now to FIG. 4, in a variation of the embodiment of FIG. 3, outer covering 16 does not comprise an opening, and flap 15 may or may not be directly attached to the outer covering. In use, flap 15 of the anchor 12 may sit along the lateral surface of the ear, while the outer covering 16 may provide an additional layer for covering the lateral surface of the ear. This variation of ear protector 10 may enhance protection of the ear.

As briefly discussed, and as described in more detail herein below with respect to FIGS. 24 and 25, during use flap 15 alternatively may be folded back towards or upon anchor 12 in the vicinity of lateral portion 14a of the opening 14, such that the opening is unobstructed and the flap is positioned against the wearer's head and/or cheek outside of chamber 18 of ear protector 10. In such a configuration, the flap may extend or project towards the anterior of the wearer's head (i.e., may extend towards the wearer's face), away from (e.g., generally perpendicular to) the tragus of the wearer's ear. When folded back towards or upon anchor 12 in this manner, flap 15 may resiliently press against the wearer's head and/or cheek in a manner that forms at least a partial seal. This seal may partially or completely block the elements, e.g., heat, cold, wind, rain and/or snow, from uncomfortably impinging upon the wearer's auricula A and/or entering the wearer's external acoustic meatus EAM. Furthermore, when used in this manner, flap 15 may facilitate placement and/or removal of the ear protector 10 during use, as also described in more detail herein below.

2. Unitary Anchor and Outer Covering

As seen in FIG. 5A, the conforming anchor 12 and outer covering 16 of ear protector 10 may be fabricated from a single piece of foamed elastomer 30, which may, for example, be cut or stamped from a sheet of the foamed elastomer. The conforming anchor 12 and outer covering 16 may, for example, meet or interface along segment 32 of the single piece 30. As seen in FIG. 5B, segment 32 may serve as a hinge along which the single piece 30 may be folded to approximate all or a portion of the outer perimeters of the anchor 12 and outer covering 16. The anchor 12 may be permanently or reversibly attached or secured to outer covering 16 (e.g., via sewing, gluing, bonding, hook-and-loop fastening or Velcroing', or any other technique) at or near all or a portion of its outer perimeter to form ear protector 10. Optionally, the ear protector may be everted prior to use to provide the ear protector with an unstressed profile that maintains chamber 18 in a relatively open configuration. Optionally, additional material layer(s) 20 may be attached to the ear protector 10, e.g., within chamber 18, to enhance insulation, waterproofing, texture, or for other reasons as desired. Optionally, the ear protector may comprise flap 15 (see, e.g., FIGS. 24-25).

Segment 32 illustratively is positioned along an interface of anchor 12 and outer covering 16 that, in use, is placed in proximity to the tragus of the ear. However, it should be understood that segment 32 alternatively may be positioned along a different interface of the anchor and outer covering, such as an interface that, in use, is placed along the helix or lobule of the ear (see, e.g., FIG. 13).

3. Ear Protector Placement/Removal Facilitators

Figure 6B:
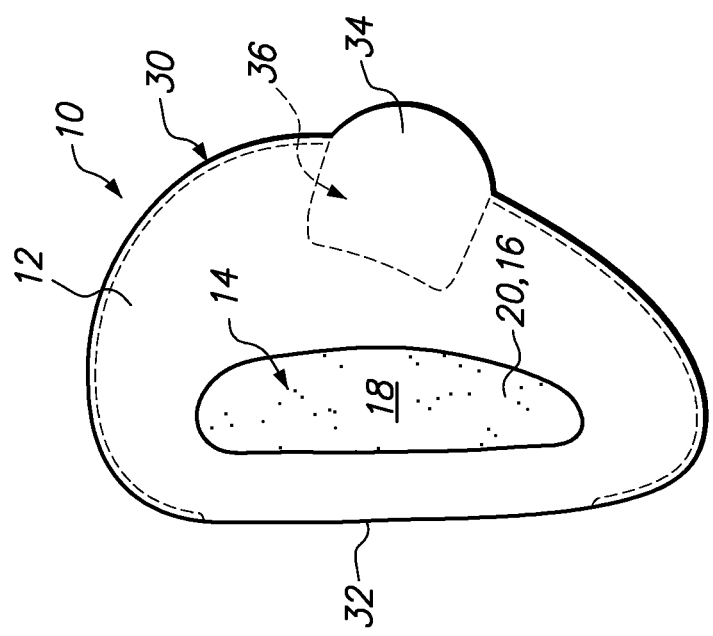

Referring now to FIG. 6, ear protector 10 optionally may comprise one or more ear protector placement/removal facilitators. For example, the ear protector may comprise a tab 34 and/or a pocket 36 to facilitate placement of the ear protector around the ear and/or removal of the ear protector, e.g. for grasping the ear protector without grasping the ear during placement or removal of the ear protector from the ear. As seen in FIG. 6A, anchor 12 may comprise tab 34, and outer covering 16 may comprise extension 37 that is formed into pocket 36. When anchor 12 and outer covering 16 are fabricated from single piece 30, as in FIG. 6, single piece 30 may be folded along segment 38 such that extension 37 lies against outer covering 16. The single piece then may be folded along segment 32, such that extension 37 is positioned between anchor 12 and outer covering 16, and such that tab 34 extends outward near segment 38. The outer perimeters of anchor 12 and outer covering 16 then may be attached to one another except along extension 37 where the anchor 12 is attached to the extension 37, but not to the outer covering 16. As seen in FIG. 6B, the attachment of anchor 12 to extension 37 moves radially inward toward opening 14 of the anchor 12 in order to form pocket 36.

In a variation of the ear protector of FIG. 6, extension 37 and/or tab 34 may be provided as separate piece(s) from single piece 30 (likewise, anchor 12 and outer covering 16 may be provided as separate pieces). The anchor 12 and outer covering 16 optionally may be attached all along their outer perimeters, and ear protector 10 may be everted to provide the unstressed profile with chamber 18 relatively open. After such optional everting of the ear protector 10, extension 37 may be attached to form pocket 36, and/or tab 34 may be attached. It should be understood that the ear protector 10 optionally may be provided with only pocket 36 or only tab 34, rather than being provided with both.

In addition or as an alternative to pocket 36 and/or tab 34, ear protector 10 may comprise other placement/removal facilitators. For example, all or a portion of the connection between anchor 12 and outer covering 16 may comprise a reversible fastener, such as hook-and-loop fastener(s) (e.g., Velcro® marketed by Velcro Industries B.V. of Amsterdam, The Netherlands), button(s), zipper(s), hook(s), snap(s), etc., to facilitate opening of all or a portion of the ear protector during placement of the protector on the ear and/or during removal of the protector from the ear. This reversible opening may facilitate grasping of a desired portion of the ear and/or of the ear protector that otherwise might not be accessible, and this may facilitate placement or removal of the ear protector.

Figure 7:
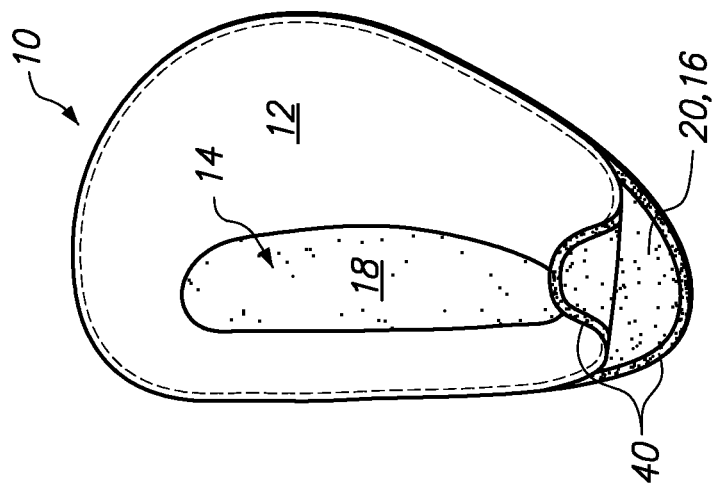
FIG. 7 is a schematic view of a variation of the ear protector embodiment of FIG. 6.

FIG. 7 illustrates one such variation of the ear protector 10 having reversible fastener 40, illustratively a hook-and-loop fastener, that reversibly connects the anchor 12 to the outer covering 16 in the vicinity of the portion of the ear protector that envelopes the lobule of the ear. During use, the wearer may open the ear protector in the lobule area, e.g., to grasp the ear lobule and place it within chamber 18. Fastener 40 then may be fastened to fully contain the auricula within chamber 18.

Figure 8:
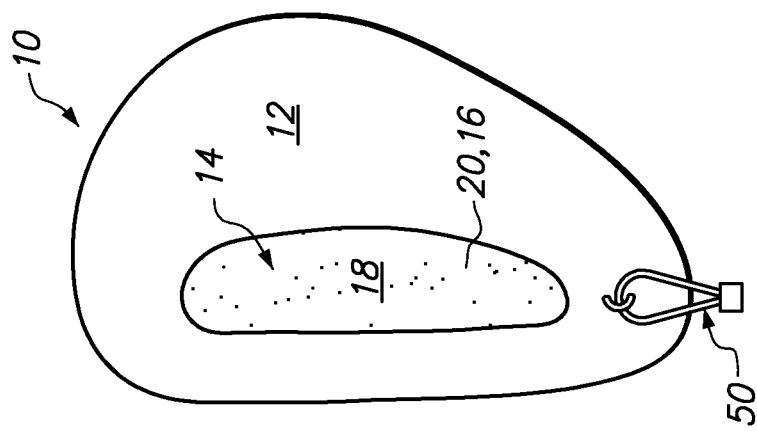
FIG. 8 is a schematic view of another variation of the ear protector embodiment of FIG. 6.

FIG. 8 illustrates an additional or alternative placement/removal facilitator comprising a pull 50 that may be utilized to resiliently deform ear protector 10 during placement on the ear or removal from the ear. In FIG. 8, pull 50 illustratively is positioned on the cranial surface of ear protector 10 (e.g., is attached to conforming anchor 12). The pull 50 additionally or alternatively may be attached to the lateral surface of the ear protector (e.g., may be attached to outer covering 16).

4. Minor Axis Symmetry

Figure 9:
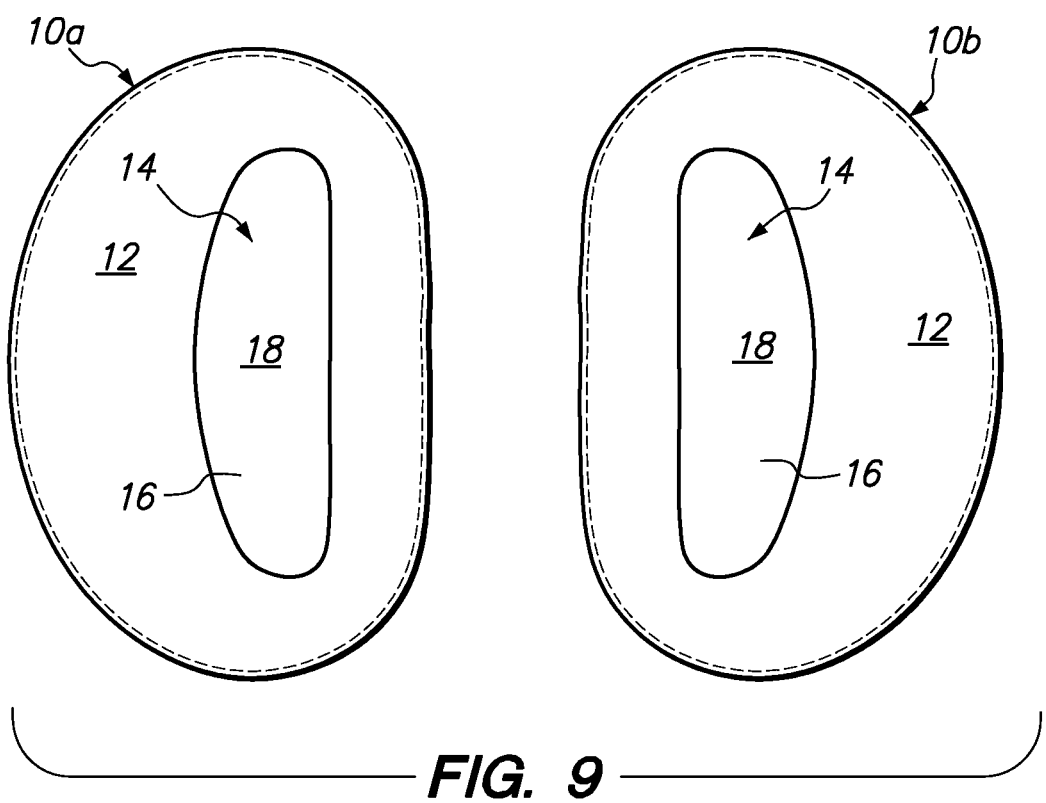
FIG. 9 is a schematic view of an embodiment of the ear protector of FIG. 2 comprising minor axis symmetry.

The ear protectors of FIGS. 2-8 comprise an outer perimeter that substantially follows the outer perimeter of the auricula. In use, this provides the ear protectors with relatively streamlined profiles that reduce or minimize that amount of material utilized to form the ear protectors, while still facilitating envelopment of external ears. However, auricula-shaped outer perimeters may require that ear protectors be fabricated specifically for use with the left or with the right ear (i.e., a given ear protector may not be used universally on either a right or left ear, as desired). In FIG. 9, a pair of ear protectors 10a and 10b are provided; each ear protector comprises symmetry about its minor axis (i.e., about the axis generally extending anterior-posterior along the wearer's head during use). Minor axis symmetry provides ear protectors 10a and 10b of FIG. 9 with universality that facilitates use of the ear protectors on either the right or the left ears, as desired.

5. Conforming Anchor in Combination with Ear Clamp

With reference to FIGS. 10 and 11, conforming anchor 12 may be utilized in combination with bistable truncated cone ear clamp 60 having opening 62 in order to secure ear protector 10 to the wearer's ear. Opening 14 of anchor 12 may conform to at least a portion of ear root R, while ear clamp 60 clamps a more outer portion of the ear between the clamp and outer covering 16, providing multiple redundant methods of stabilizing the ear protector on the ear without external support. Such redundancy optionally may facilitate use of an ear clamp 60 providing less clamping force than would be required to stabilize the ear protector without such redundancy (i.e., when utilizing only an ear clamp to stabilize the ear protector, rather than using ear clamp 60 in combination with opening 14 of anchor 12 as in FIGS. 10 and 11), which may provide enhanced comfort to the wearer.

As seen in FIG. 10A, ear clamp 60 may, for example, be fabricated from a rigid or semi-rigid material, such as a plastic. The plastic may, for example, comprise low-density polyethylene ("LDPE"), polycarbonate ("PC"), or polyvinyl chloride ("PVC"); more preferably, the plastic may, for example, comprise polypropylene ("PP") or high-density polyethylene ("HDPE"). The plastic may, for example, comprise a thickness in the range of about 0.01"-0.08" (e.g., a thickness in the range of about 0.25 mm-2 mm), more preferably a thickness in the range of about 0.025"-0.06" (e.g., a thickness in the range of about 0.6 mm-1.5 mm), even more preferably a thickness in the range of about 0.035"-0.06" (e.g., a thickness in the range of about 0.9 mm-1.5 mm).

Ear clamp 60 may be fabricated via injection molding or via thermoforming of a sheet of the rigid or semi-rigid material. Alternatively, as seen in FIG. 10A, the ear clamp 60 may be cut or stamped in a "C"-shape from a flat sheet of the material, and the ends of the "C"-shape may be approximated or overlapped and secured (e.g., taped, sewn, stapled, glued, bonded, hook-and-loop fastened or otherwise secured)— illustratively, stapled and taped with tape 64—to form the bistable truncated cone, with the overlapped/ secured portion preferably configured for placement in the vicinity of the wearer's tragus T during use.

Optionally, as also seen in FIG. 10A, the conforming anchor 12 also may be cut or stamped in a "C"-shape, and the ends of the conforming anchor also may be approximated and secured (e.g., taped, sewn, stapled, glued, bonded, hook-and-loop fastened or otherwise secured) in order to form opening 14 and provide the anchor with a truncated cone profile suitable for attachment to the ear clamp 60. In FIG. 10A, anchor 12 has been cut or stamped such that the approximated ends of the anchor are positioned along the lateral portion 14a of the opening 14; however, it should be understood that the anchor alternatively may be cut or stamped such that the approximated ends of the anchor are positioned along some other portion of the opening 14, such as along the cranial portion 14b of the opening (e.g., the anchor may be cut or stamped in a backwards "C"-shape). It also should be understood the anchor 12 may be provided with a truncated cone profile (e.g., may be cut or stamped in a "C"-shape with approximated and secured ends) even when ear protector 10 does not comprise a bistable truncated cone ear clamp. Providing anchor 12 with such a profile may maintain chamber 18 in a relatively open configuration that facilitates placement of the wearer's ear within the chamber.

As seen in FIG. 10B, ear clamp 60 may be attached to conforming anchor 12 (e.g., sewn, glued, bonded or otherwise secured; such attachment may be provided in addition, or as alternative, to attachment of the approximated ends of the "C"-shaped anchor to one another), and outer covering 16 may be attached to the outer perimeter of the anchor 12 and/or to the ear clamp 60. Opening 62 of the ear clamp 60 is larger than opening 14 of anchor 12, such that the relatively rigid edge of opening 62 is set back from the conforming edge of anchor opening 14 along its cranial portion 14b. Ear clamp 60 illustratively is positioned within chamber 18 of ear protector 10, but it should be understood that the ear clamp alternatively may be positioned closer to the wearer's cranium than is conforming anchor 12 (i.e., the relative positions of anchor 12 and ear clamp 60 may be reversed). Optional additional material layer(s) 20 may be positioned between ear clamp 60 and the wearer's ear during use, such that ear clamp 60 is fully enclosed within the ear protector 10.

As seen in FIG. 11A, in use, ear clamp 60 is placed in its convex configuration such that chamber 18 is relatively open to receive auricula A. Opening 14 of conforming foamed elastomer anchor 12, which is smaller than opening 62 of bistable (semi-) rigid ear clamp 60, is resiliently deformed during passage of auricula A through openings 14 and 62 into chamber 18. Upon placement of the auricula A within chamber 18, opening 14 resiliently conforms to at least a portion of ear root R, while ear clamp 60 is set back from the ear root along the cranial portion 14b of the anchor's opening 14. As seen in FIG. 11B, ear clamp 60 then is everted to a concave configuration, e.g., by the wearer grasping the top and bottom of the ear protector 10 along its major axis and flexing the ear protector to evert it.

In the concave configuration of the FIG. 11B, ear clamp 60 clamps a portion of the ear between the ear clamp and outer covering 16, while the opening 14 of the conforming foamed elastomer anchor 12 conformably engages at least a portion of the ear root R. The combination of ear root engagement provided by anchor 12 and ear clamping provided by ear clamp 60 may provide a more stable reversible attachment of ear protector 10 to auricula A than would the anchor 12 or the ear clamp 60 in isolation. After use, the ear clamp 60 optionally may be everted back to the convex configuration to reopen chamber 18 and facilitate removal of the ear protector from the wearer's ear.

FIGS. 10 and 11 illustrate a combination ear clamp/ conforming anchor embodiment of ear protector 10 exhibiting symmetry about its minor axis. However, it should be understood that such a combination ear clamp/conforming anchor alternatively may be provided in an embodiment of the ear protector that does not exhibit minor axis symmetry, e.g., that has an outer perimeter that mimics the outer perimeter of the auricula A. As seen in FIG. 12, in such a variation of the embodiment of FIGS. 10 and 11, ear clamp 60 also may comprise an outer perimeter that mimics the outer perimeter of the auricula.

6. Outer Covering Attachment to the Anchor Along the Lateral Portion of the Anchor Opening In some embodiments, attachment of the anchor 12 to outer covering 16 along the outer perimeter of the anchor in the vicinity of lateral portion 14a of the anchor's opening 14 may cause the outer covering 16 to pull anchor 12 and ear protector 10 away from the wearer's cheek/head near the tragus T of the wearer's ear (i.e., between the lateral portion 14a of opening 14 and the outer perimeter of anchor 12). This can create a small air gap between the ear protector and the wearer's head near the tragus T of the wearer's ear, which may expose the ear to some amount of wind and/or other elements.

After substantial experimentation and prototyping, we have discovered that this air gap may result from chamber 18 extending radially outward beyond lateral portion 14a of opening 14 to the outer perimeter of anchor 12, thereby extending the chamber 18 beyond the wearer's auricula A near the tragus T. When the outer covering comprises a foamed elastomer or other resilient material, such extension of chamber 18 beyond lateral portion 14a of opening 14 may apply a force to the outer perimeter of the anchor 12 in the vicinity of the lateral portion 14a of opening 14 that pulls the anchor away from the wearer's cheek/head during use.

In some embodiments, a more flush or sealing fit of the ear protector 10 against the wearer's head in the vicinity of the tragus T may be achieved by attaching the outer covering 16 to anchor 12 at or near all or a segment of the lateral portion 14a of opening 14, in addition or as an alternative to attachment of the outer covering to the anchor along the outer perimeter of the anchor in the vicinity of the lateral portion 14a. Attachment of the outer covering 16 to the anchor 12 at or near all or a segment of the lateral portion 14a of the opening 14 terminates chamber 18 near all or a segment of the lateral portion 14a, which sits along the origin of the tragus T during use. In the vicinity of the attachment of the outer covering 16 to all or a segment of lateral portion 14a of opening 14 of anchor 12, the outer covering 16 may further extend to the outer perimeter of the anchor 12, may terminate at or near its attachment to all or a segment of the lateral portion 14a, and/or may terminate anywhere between the lateral portion 14a and the outer perimeter of anchor 12.

With reference now to FIG. 13, an illustrative embodiment of ear protector 10 is described comprising outer covering 16 attachment along all or a segment of the lateral portion 14a. FIG. 13 also illustrate a method of manufacturing such an ear protector 10. The ear protector 10 of FIG. 13 illustratively comprises minor axis symmetry, a unitary anchor and outer covering attached along a segment that is configured for placement in proximity to the helix of the wearer's ear, an additional layer of material 20 attached to the outer covering 16, and an optional method of manufacture comprising everting of the anchor and outer covering. However, it should be understood that the ear protector 10 with outer covering 16 attached along all or a segment of the lateral portion 14a may comprise any desired combination of ear protector features, profiles, designs, manufacture methods, etc., described previously or known in the art.

Figure 13A:
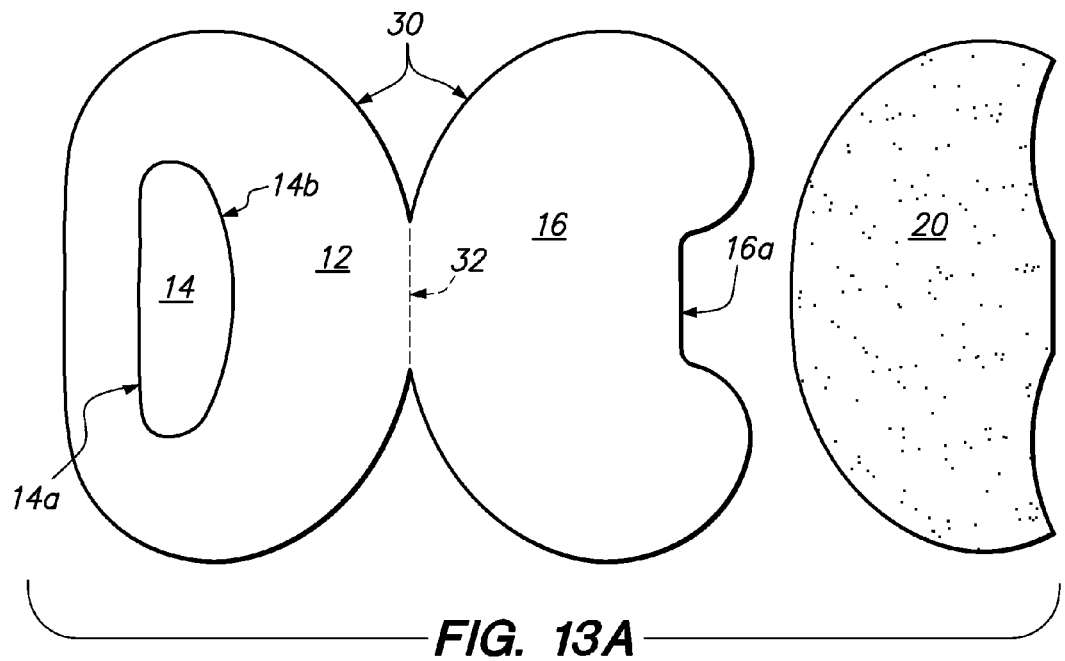
FIGS. 13A-13D are schematic views illustrating a method of manufacture and an embodiment of the ear protector of FIG. 2 comprising attachment of the outer covering to the anchor along the lateral portion of the anchor opening.

As seen in FIG. 13A, the conforming anchor 12 and outer covering 16 of ear protector 10 optionally may be fabricated from a single piece of foamed elastomer 30, which may, for example, be cut or stamped from a sheet of the foamed elastomer. The conforming anchor 12 and outer covering 16 may, for example, meet along segment 32 that is configured for placement along a portion of the helix of the ear during use. As will be apparent, conforming anchor 12 and outer covering 16 alternatively may comprise separate elements that subsequently are secured to one another.

Outer covering 16 illustratively comprises segment 16a that is configured for attachment along all or a segment of lateral portion 14a of opening 14 of anchor 12. In FIG. 13, outer covering 16 terminates along segment 16a. Additionally, the segment 16a illustratively extends along only a portion of the outer covering about the outer covering's major axis (i.e., the segment 16a does not extend to the outer perimeter of the outer covering lengthwise along the outer covering's major axis); this may provide chamber 18 of ear protector 10 with additional space for comfortably accommodating a wearer's ear helix H and/or lobule L within the chamber. It should be understood that outer covering 16 alternatively may extend radially outward in the direction of the outer covering's minor axis beyond segment 16a, e.g., may extent part or all of the way to the outer perimeter of the anchor 12 along its minor axis (see, for example, FIGS. 14A and 14B). Furthermore, segment 16a may extend lengthwise in the direction of the outer covering's major axis beyond lateral portion 14a of anchor 12, e.g., may extend part or all of the way to the outer perimeter of the anchor 12 along its major axis (see, for example, FIG. 14C).

Figure 13B:
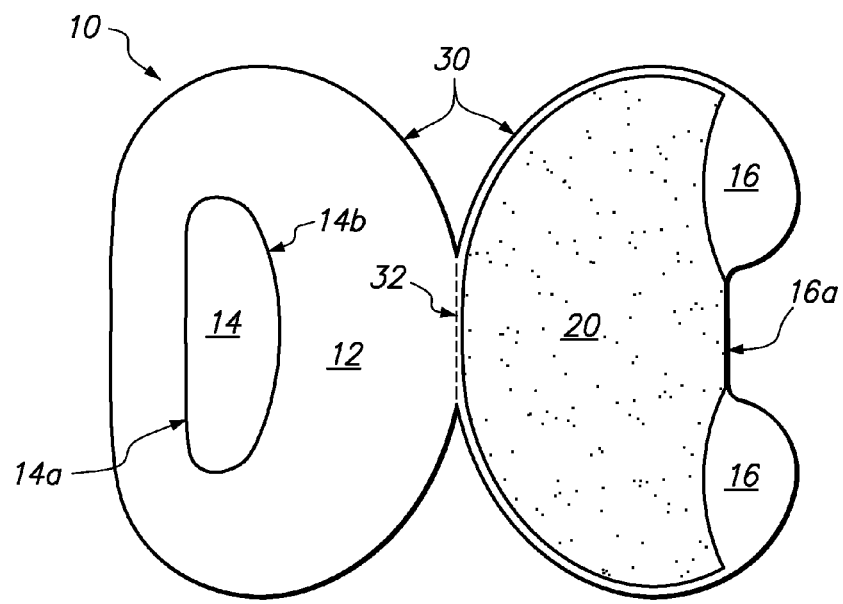

Ear protector 10 illustratively also comprises additional material layer 20 (e.g., fleece layer 20), which may enhance thermal insulation or waterproofing, may provide a desired texture, etc. As seen in FIG. 13B, material layer 20 may be secured (e.g., sewn, glued, bonded or otherwise connected) to outer covering 16. Material layer 20 illustratively is slightly undersized relative to outer covering 16, e.g., to facilitate attachment of anchor 12 directly to the outer covering 16 without layer 20 positioned between the anchor and the outer covering. Direct attachment of the outer covering to the anchor without an intervening layer of material 20 may reduce relative thickness in the vicinity of the attachment of the anchor to the outer covering. Such reduced relative thickness may facilitate everting of the anchor and outer covering during manufacture to provide ear protector 10 with an unstressed profile that maintains chamber 18 in a relatively open configuration that facilitates placement of the auricula A within the chamber. It should be understood that layer 20 alternatively may be comparably sized to outer covering 16 and optionally may be attached to both outer covering 16 and anchor 12 along all or a portion of the attachment line connecting the outer covering to the anchor.

In FIG. 13B, material layer 20 also illustratively does not extend to the outer perimeter of the outer covering 16 proximal and distal of segment 16a. This may locally increase the volume of chamber 18 of ear protector 10 to facilitate comfortable accommodation of a wearer's ear helix H and/or lobule L within the chamber. It should be understood that material layer 20 alternatively may extend to or near the outer perimeter of the outer covering 16 proximal and distal of segment 16a. Furthermore, one or more additional or alternative material layers may be attached to anchor 12.

Figure 13C:
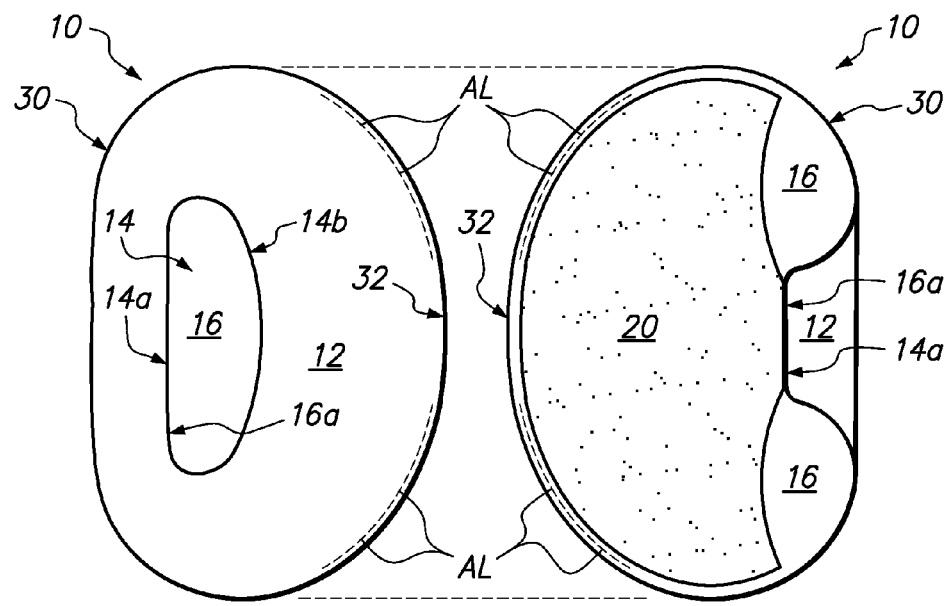

Referring now to FIG. 13C, single piece 30 may be folded along segment 32 to approximate at least a portion of the outer perimeters of the anchor 12 and outer covering 16. The outer perimeters of anchor 12 and outer covering 16 are partially secured (e.g., sewn, glued, bonded, hook-and-loop fastened or 'Velcroed', or otherwise connected) to one another along attachment edge or line AL, approximately between the ends of segment 32 to points roughly parallel with the beginning of cranial surface 14b of opening 14 of anchor 12 along the minor axis of the ear protector. As will be apparent, prior to attachment of material layer 20 to outer covering 16, the outer perimeters of anchor 12 and outer covering 16 may be partially secured along attachment line AL, and/or segment 32 may be folded.

When the anchor and outer covering subsequently are everted, as illustratively shown in the method of manufacture of FIG. 13, material layer 20 initially is positioned on the outside of outer covering 16 as in FIG. 13C, rather than between the outer covering and anchor 12. Material layer 20 is placed within chamber 18 by everting the anchor and the outer covering, as in FIG. 13D. It should be understood that ear protector 10 alternatively may be fabricated without everting the anchor and outer covering, in which case the material layer(s) 20 initially would be positioned between the outer covering and the anchor for placement within chamber 18.

Figure 13D:
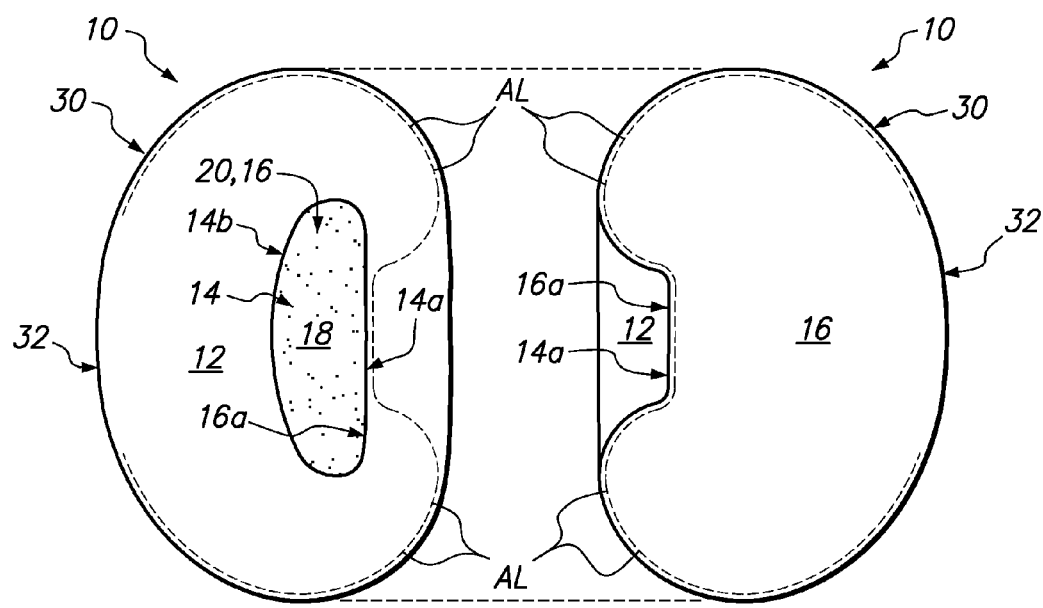

As seen in FIG. 13D, the partially assembled ear protector 10 is everted along attachment line AL of FIG. 13C, which creates a partially formed chamber 18 with an unstressed profile that maintains the partially formed chamber 18 in a relatively open configuration. Everting the partially assembled ear protector also places material layer 20 within partially formed chamber 18. Attachment line AL then is extended, illustratively along the outer perimeter of the outer covering 16, to fully form ear protector 10 with chamber 18. The ear protector may be resiliently deformed, attached to the ear and utilized as discussed previously with regard to earlier embodiments.

The profile of the attachment line AL, as well as the fold line along segment 32, defines the perimeter of chamber 18. Segment 16a of the outer covering 16 is attached to anchor 12 near a segment of lateral portion 14a of opening 14, such that chamber 18 terminates at or near at least a segment of the lateral portion 14a of opening 14. As discussed previously, such termination of the chamber 18 at or near at least a segment of the lateral portion 14a of opening 14 may provide a more flush and sealed fit of the ear protector 10 against the wearer's cheek/head in the vicinity of the tragus T during use.

Referring now to FIG. 14, in the vicinity of lateral portion 14a of opening 14 of anchor 12, the outer covering 16 may terminate at or near segment 16a and the segment's attachment to all or a segment of the lateral portion 14a, as in FIG. 13; may extend to the outer perimeter of the anchor 12 along the ear protector's minor axis; and/or may terminate anywhere between the lateral portion 14a and the outer perimeter of anchor 12. Furthermore, segment 16a may extend lengthwise in the direction of the outer covering's major axis beyond lateral portion 14a of anchor 12, e.g., may extend part or all of the way to the outer perimeter of the anchor 12 along its major axis.

Figure 14A:
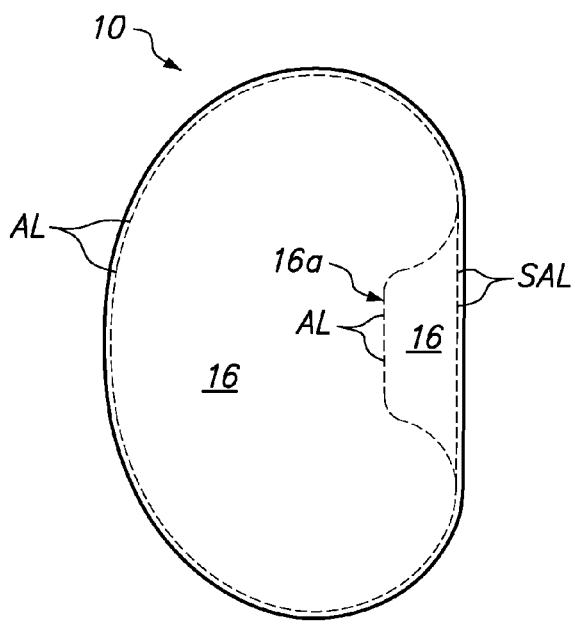
FIGS. 14A-14C are schematic views of variations of the ear protector embodiment of FIG. 13.

FIG. 14A illustrates a variation of ear protector 10 of FIG. 13 wherein the outer perimeter of the outer covering 16 extends along the ear protector's minor axis to the outer perimeter of the anchor 12 in the vicinity of the lateral portion 14a of the opening 14 of anchor 12. Attachment line AL secures segment 16a of outer covering 16 near all or a segment of lateral portion 14a of anchor opening 14, while optional second attachment line SAL secures the outer covering 16 to the anchor 12 along their outer perimeters in the vicinity of the lateral portion 14a. In the variation of FIG. 14A, the anchor 12 and outer covering 16 illustratively are shown as separate elements that have been joined together along attachment line AL and second attachment line SAL, rather than as a unitary element fabricated from single piece 30; it should be understood that the anchor and outer covering alternatively may comprise a unitary element.

Figure 14B:
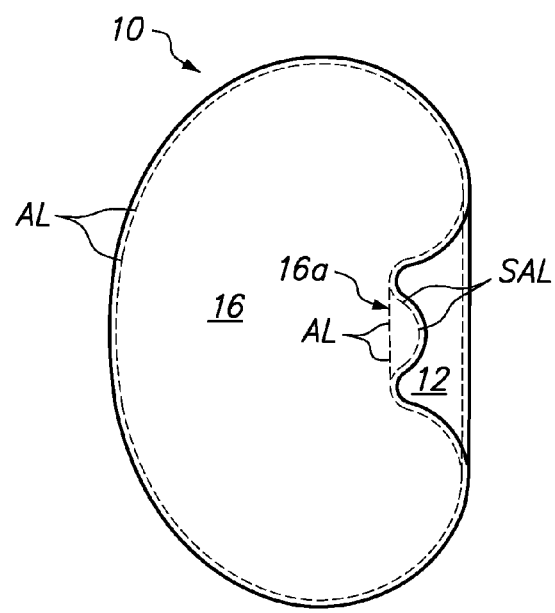

FIG. 14B illustrates another variation of ear protector 10 of FIG. 13 wherein the outer perimeter of the outer covering 16 terminates between the lateral portion 14a of opening 14 and the outer perimeter of anchor 12 in the vicinity of the lateral portion 14a along the ear protector's minor axis. Again attachment line AL secures segment 16a of outer covering 16 near all or a segment of lateral portion 14a of anchor opening 14, while optional second attachment line SAL secures the outer perimeter of the covering 16 to the anchor 12 in the vicinity of the lateral portion 14a between the lateral portion 14a and the outer perimeter of anchor 12.

Figure 14C:
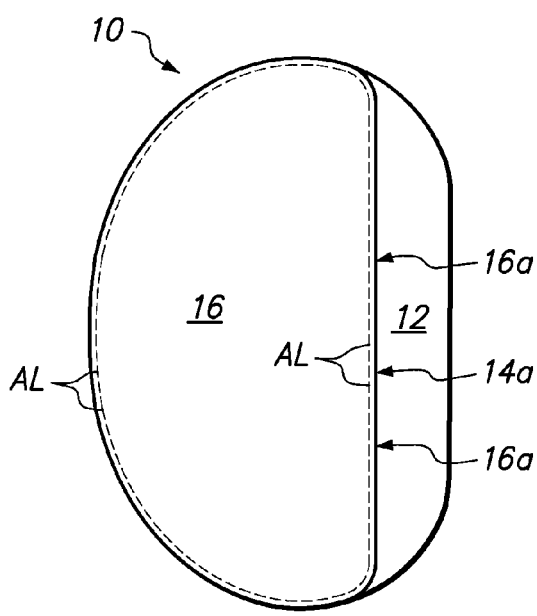

FIG. 14C illustrates yet another variation of the ear protector 10 of FIG. 13 wherein the segment 16a of outer covering 16 extends lengthwise in the direction of the ear protector's major axis beyond lateral portion 14a of anchor 12, illustratively all the way to the outer perimeter of the anchor 12 along the ear protector's major axis. Attachment line AL secures segment 16a of outer covering 16 along all of lateral portion 14a of anchor opening 14. In FIG. 14C, outer covering 16 illustratively terminates along its extended segment 16a, though it should be understood that the outer covering alternatively may extend further outward along the ear protector's minor axis, as in the variations of FIG. 13, 14A and 14B, in which case the outer covering optionally could be secured to the anchor along an optional second attachment line SAL, as in FIGS. 14A and 14B.

Ear protector 10 of FIG. 14C may comprise a chamber 18 with relatively less space for accommodating the wearer's ear helix and/or lobule, as compared to the ear protector variations of FIG. 13 and FIGS. 14A and 14B. This may provide a more snug fit during use but may also require additional stretching/resilient deformation of the ear protector to position the wearer's ear within chamber 18.

Figure 15A:
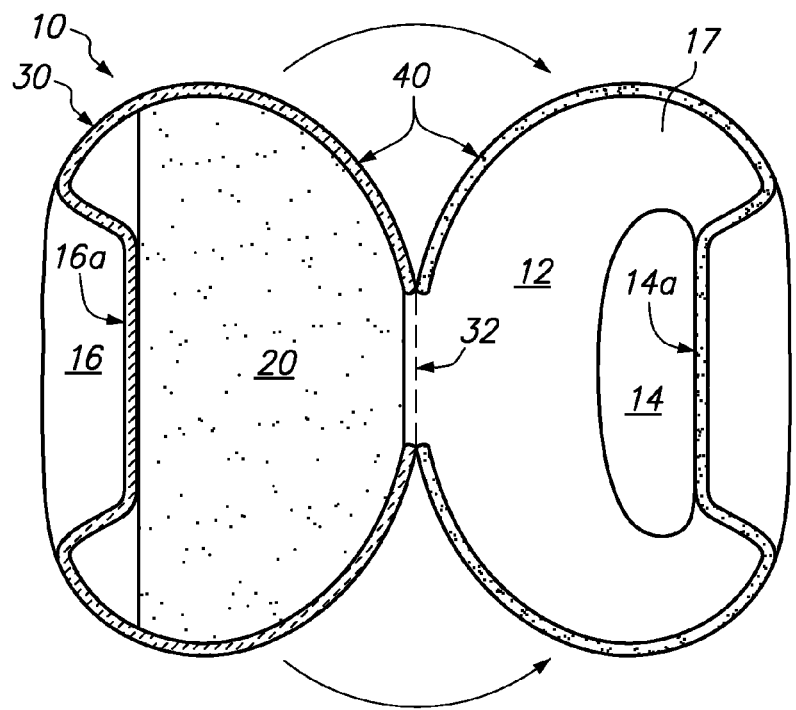
FIGS. 15A and 15B are schematic views of a variation of the ear protector embodiment of FIG. 13 comprising placement/removal facilitators in combination with outer covering attachment to the anchor along the lateral portion of the anchor opening.
Figure 15B:
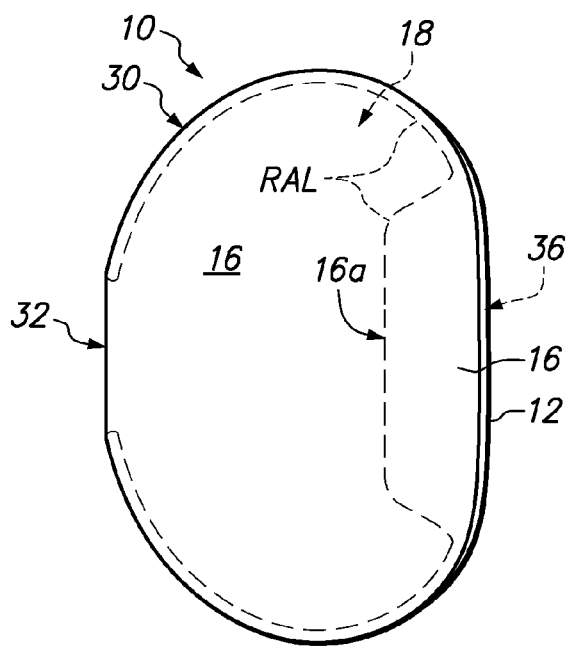

Referring now to FIGS. 15-20, it may be desirable to provide ear protector 10 with placement/removal facilitators (as described previously, for example, with respect to FIGS. 6-8), in combination with outer covering attachment to the anchor along all or a segment of the lateral portion of the anchor opening. FIGS. 15 and 16 illustrate an embodiment and a method of using such an ear protector 10 comprising reversible fastener 40 positioned along reversible attachment line RAL, which facilitates formation of chamber 18 after placement of the wearer's auricula A through opening 14 of anchor 12. This may simplify placement of the wearer's ear within chamber 18 of the ear protector.

As seen in FIG. 15A, anchor 12 and outer covering 16 optionally may be fabricated as a unitary element from single piece 30 of foamed elastomer. The anchor and outer covering meet at segment 32, which illustratively is configured for placement along a portion of the helix of the ear during use (segment 32 alternatively may be configured for placement along some other portion of the ear during use, for example, along a portion of the tragus of the ear during use, as in FIGS. 18-20). The segment 32 serves as a hinge that may resiliently open single piece 30 to a relatively flat profile as in FIG. 15A, when the reversible fastener 40 is not fastened along all or a portion of reversible attachment line RAL. The outer covering 16 may be reversibly fastened to the anchor 12 along the reversible attachment line RAL to form chamber 18 of ear protector 10.

Reversible fastener 40, positioned along reversible attachment line RAL for reversibly fastening the outer covering 16 to the anchor 12, illustratively comprises a hook-and-loop fastener (e.g., a Velcro® fastener, marketed by Velcro Industries B.V. of Amsterdam, The Netherlands), though it should be understood that button(s), zipper(s), hook(s), snap(s), or any other reversible fasteners alternatively may be used, as desired. Optionally, the hook component and/or the loop component of reversible hook-and-loop fastener 40 may comprise a low profile or molded fastener, such as an Ultra-Mate® Velcro® fastener (Velcro Industries B.V., Amsterdam, The Netherlands). A low profile or molded hook-and-loop fastener may provide a smoother interface as compared to a standard hook-and-loop fastener, which may be more comfortable should reversible fastener 40 come into contact with the wearer's ear or head.

Optionally, the backing material 17 applied to the interior (and/or exterior) surface of anchor 12 and/or to outer covering 16 may comprise the hook component and/or the loop component of the hook-and-loop fastener. In such an embodiment, reversible fastener 40 may comprise only the hook component or only the loop component of the hook-and-loop fastener, which may be attached only to the anchor 12 or only to the outer covering 16. For example, the interior surface backing material 17 of foamed elastomer single piece 30 (i.e., the backing material attached to the surface of single piece 30 that is positioned in proximity to the wearer's ear within chamber 18 during use of ear protector 10) may comprise a loop-type or unbreakable loop-type ("UBL") backing material, while the hook component reversible fastener 40 may be attached only to the anchor 12 or only to the outer covering 16. In such an embodiment, the hook component reversible fastener 40 may be configured to reversibly engage and attach to the loop component backing material 17 when single piece 30 is folded over upon itself along segment 32 to form the ear protector 10 (see, for example, FIGS. 24-25).

Figure 16A:
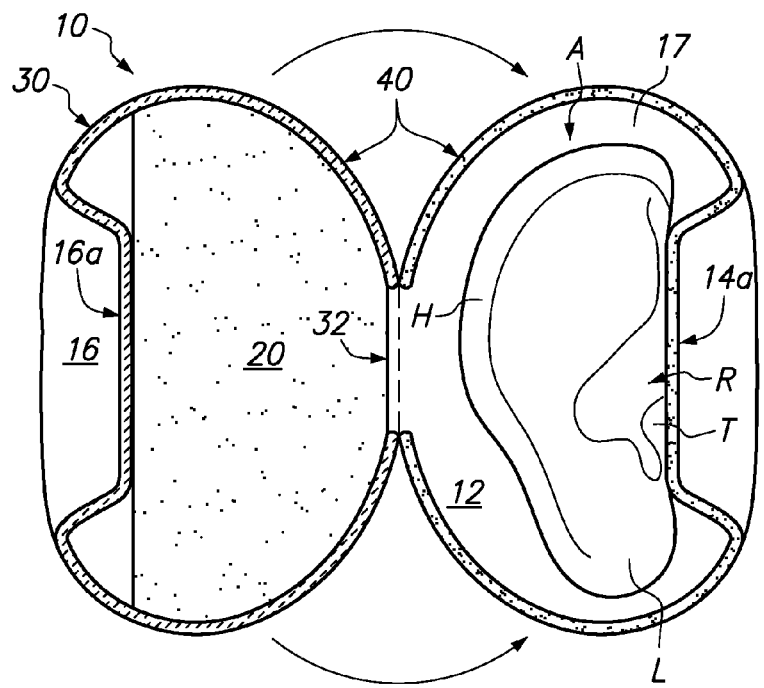
FIGS. 16A and 16B are schematic views illustrating a method of using the ear protector of FIG. 15.
Figure 16B:
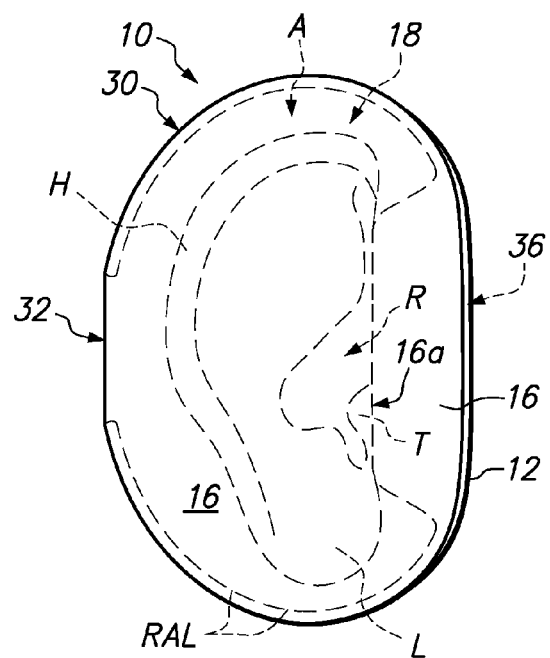

In use, the wearer's ear may be placed through opening 14 of anchor 12 while the ear protector 10 is in a partially open configuration or in a completely open configuration, as seen in FIG. 16A. This open configuration may facilitate grasping of a desired portion of the auricula A and/or of the ear protector that otherwise would not be accessible, such as the ear helix H or lobule L, which may facilitate passage or removal of the ear through the opening 14. After passage of the ear through the opening, single piece 30 may be folded along segment 32 to approximate the outer covering 16 and the anchor 12, illustratively in the vicinity of the wearer's tragus T, as in FIG. 16B. The outer covering 16 may be reversibly secured to the anchor 12 along reversible attachment line RAL via reversible fastener 40. This forms chamber 18 with the wearer's ear protected therein. During removal of the ear protector 10 from the wearer's ear, the ear protector may be maintained in the configuration of FIG. 16B, or all or a portion of the reversible attachment of the outer covering to the anchor along reversible attachment line RAL may be detached (e.g., the hook-and-loop fastener may be partially or fully separated) to facilitate removal.

In the embodiment of FIGS. 15 and 16, reversible attachment of the outer covering to the anchor along the reversible attachment line RAL also illustratively forms optional pocket 36 in the vicinity of segment 16A of outer covering 16 and lateral portion 14a of opening 14 of anchor 12. Pocket 36 may facilitate grasping of the ear protector and/or opening of the ear protector back to the profile of FIGS. 15A and 16A. Optionally, reversible fastener 40 also may extend along a second (reversible) attachment line SAL, as in FIG. 14A, for selective sealing of pocket 36.

As will be apparent, anchor 12 and outer covering 16 optionally may be fabricated as separate elements. In such a variation, the anchor and the outer covering may be permanently attached to one another where segment 32 otherwise would be located (e.g., via sewing, gluing, bonding, etc.). Alternatively, in such a variation reversible attachment line RAL with reversible fastener 40 optionally may extend along the region where segment 32 otherwise would be positioned, and the anchor and outer covering optionally may be completely detached from each other: the wearer's ear would be placed through the opening 14 of anchor 12 while the outer covering 16 were detached, and the outer covering 16 then would be reversibly attached to the anchor 12 via reversible fastener 40 along reversible attachment line RAL to form chamber 18 and ear protector 10.

Figure 17:
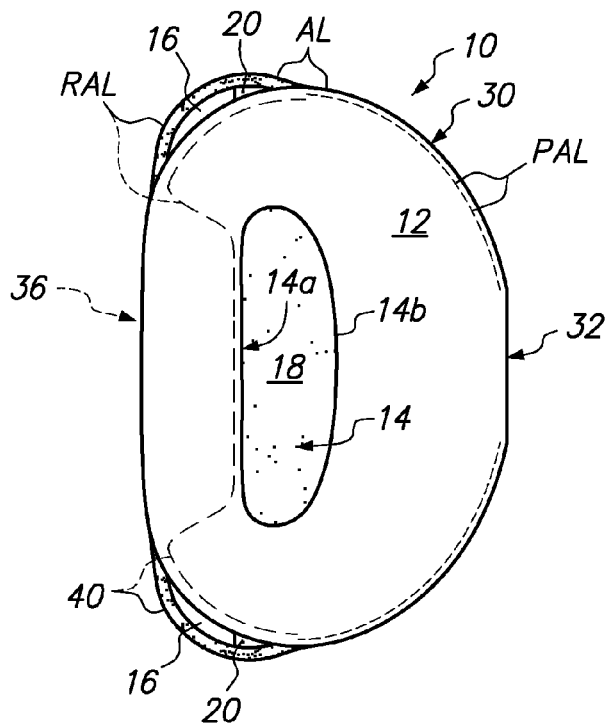
FIG. 17 is a schematic view of a variation of the ear protector of FIG. 15.

FIG. 17 illustrates a variation of the ear protector 10 of FIGS. 15 and 16. In FIG. 17, the attachment line AL connecting the outer covering 16 to the anchor 12 during use partially comprises permanent attachment line PAL (e.g., the outer covering 16 and the anchor 12 may be sewn, bonded or otherwise permanently attached to one another along the permanent attachment line PAL) and partially comprises reversible attachment line RAL with reversible fastener 40. The permanent attachment line PAL illustratively is configured for placement in proximity to the wearer's helix H and partially forms chamber 18.

FIG. 17 illustrates an open configuration of the ear protector 10, which facilitates placement of the wearer's ear through opening 14 of the anchor 12 into the partially formed chamber 18. After placement of the wearer's ear into the partially formed chamber, outer covering 16 may be reversibly attached to anchor 12 along the reversible attachment line RAL (i.e., the portion of the attachment line AL comprising reversible fastener 40) via reversible fastener 40, thereby fully forming chamber 18 with the wearer's ear protected therein. As will be apparent, the ear protector of FIG. 15 optionally may be positioned in a similar configuration to the ear protector of FIG. 17 during passage of the wearer's ear through opening 14 of the anchor 12 into chamber 18 by partially attaching the anchor 12 to the outer covering 16 along reversible attachment line RAL via reversible fastener 40.

Figure 18A:
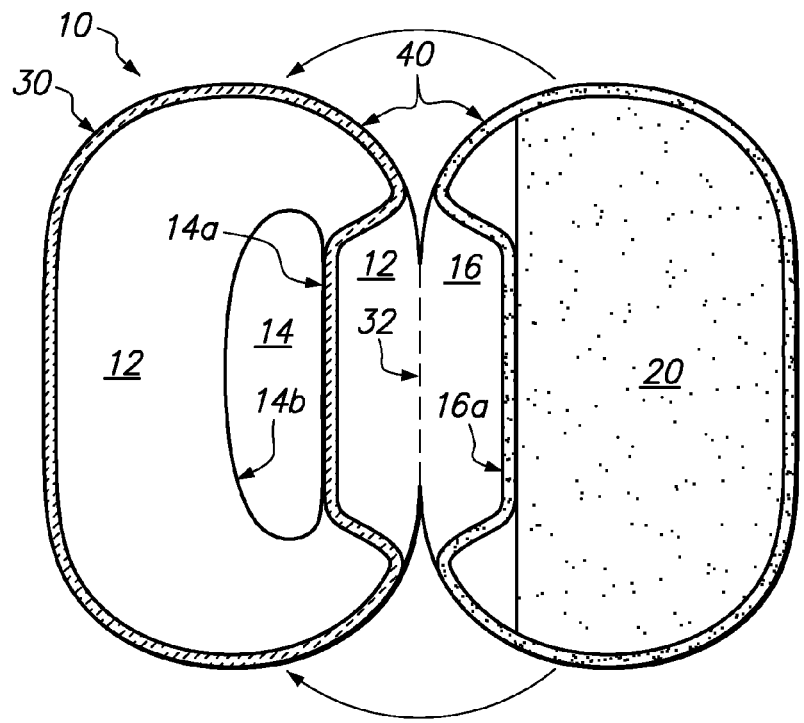
FIGS. 18A and 18B are schematic views of another variation of the ear protector of FIG. 15.
Figure 18B:
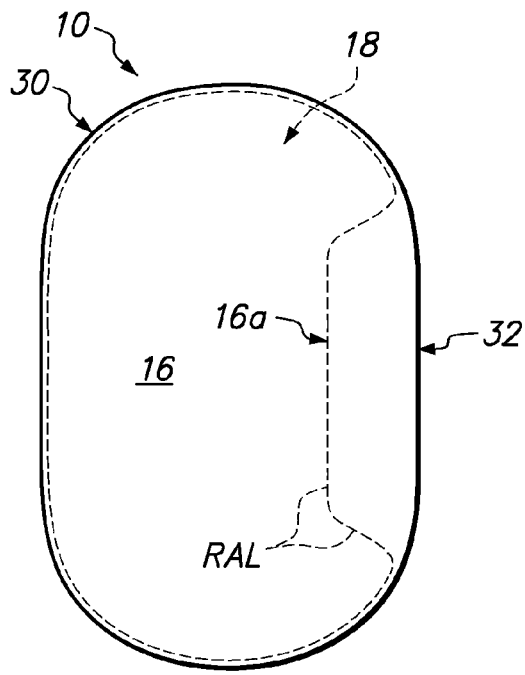

With reference now to FIGS. 18 and 19, another variation of the ear protector 10 of FIGS. 15 and 16 is described. In FIG. 18, the anchor 12 and outer covering 16 again illustratively are fabricated as a unitary element from single piece 30 of foamed elastomer. The anchor and outer covering meet at segment 32 that illustratively is configured for placement along at least a portion of the tragus T of the wearer's ear during use, rather than along the helix H, as in FIGS. 15 and 16. Ear protector 10 again comprises reversible fastener 40 (illustratively a hook-and-loop fastener, though any other reversible fastener may be utilized), positioned along reversible attachment line RAL (preferably including at least a segment of lateral portion 14a of opening 14 of anchor 12 in order to reduce air gaps, as described previously). FIG. 18A illustrates the open configuration that facilitates placement of the wearer's ear through opening 14 of the anchor 12, while FIG. 18B illustrates the closed configuration where the outer covering 16 is reversibly attached to the anchor 12 along the reversible attachment line RAL, forming chamber 18. Between the open configuration of FIG. 18A and the closed configuration of FIG. 18B are partially open and partially closed configurations, which also may be utilized during placement and/or removal of ear protector 10.

Figure 19A:
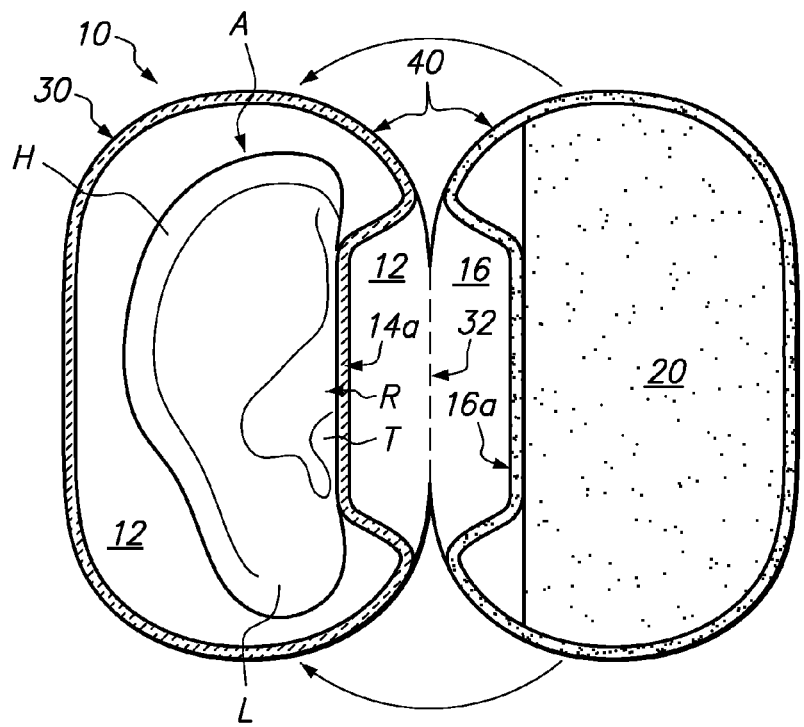
FIGS. 19A and 19B are schematic views illustrating a method of using the ear protector of FIG. 18.
Figure 19B:
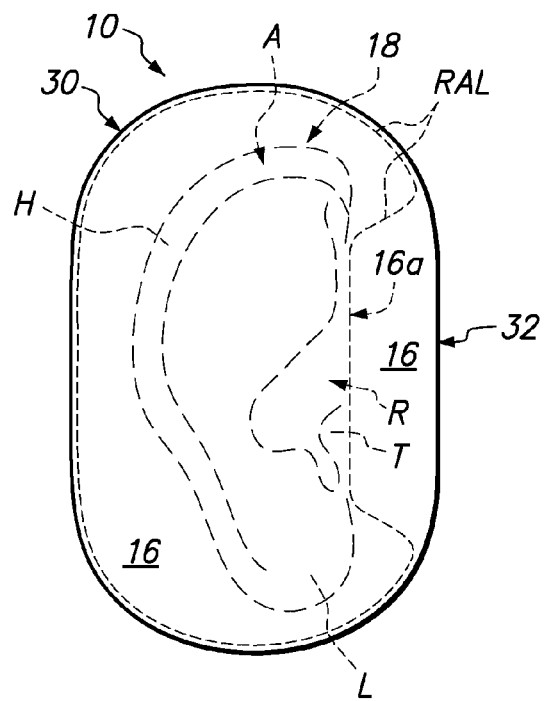

In use, the wearer's ear may be passed through opening 14 of anchor 12 while the ear protector 10 is in the fully open configuration, as seen in FIG. 19A, or is in a partially open configuration. Utilizing a partially or fully open configuration may facilitate grasping of a desired portion of the auricula A and/or of the ear protector that otherwise would not be accessible, such as the ear helix H or lobule L, which may facilitate placement or removal of the ear through the opening 14. After placement of the ear through the opening, single piece 30 may be folded along segment 32 to approximate the outer covering 16 and the anchor 12 in the vicinity of the wearer's helix H, as in FIG. 19B. The outer covering 16 may be reversibly secured to the anchor 12 along reversible attachment line RAL via reversible fastener 40. This forms chamber 18 with the wearer's ear protected therein. During removal of the ear protector 10 from the wearer's ear, the ear protector may be maintained in the configuration of FIG. 19B, or all or a portion of the reversible attachment of the outer covering to the anchor along reversible attachment line RAL may be detached (e.g., the hook-and-loop fastener may be partially or fully separated) to facilitate removal.

Figure 20:
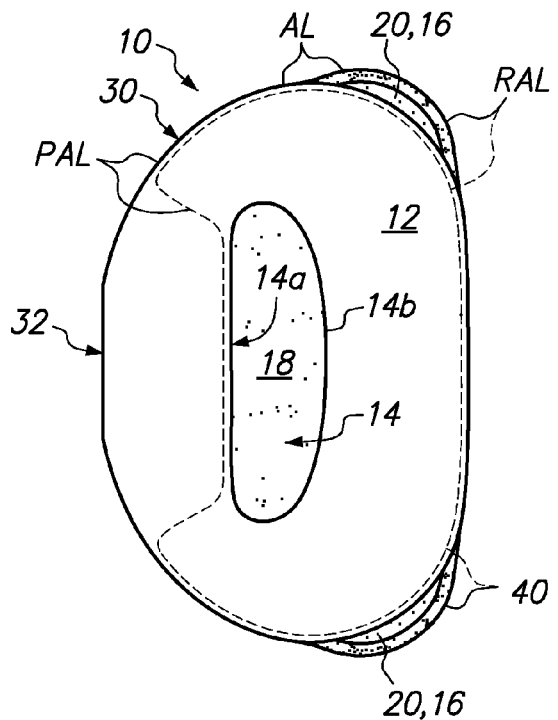
FIG. 20 is a schematic view of a variation of the ear protector of FIG. 18.

FIG. 20 illustrates a variation of the ear protector 10 of FIGS. 18 and 19. In FIG. 20, the attachment line AL connecting outer covering 16 to anchor 12 during use partially comprises permanent attachment line PAL and partially comprises reversible attachment line RAL with reversible fastener 40. The outer covering 16 and the anchor 12 are permanently attached to one another along the permanent attachment line PAL that is configured for placement in proximity to the wearer's tragus T and that partially forms chamber 18. FIG. 20 illustrates the open configuration of the ear protector that facilitates placement of the wearer's ear through opening 14 of the anchor 12 into partially formed chamber 18, after which the outer covering 16 may be reversibly attached to the anchor 12 along the reversible attachment line RAL (i.e., the portion of the attachment line AL comprising reversible fastener 40) to fully form chamber 18 with the wearer's ear protected therein. As will be apparent, the ear protector of FIG. 18 optionally may be positioned in a similar configuration to the ear protector of FIG. 20 during passage of the wearer's ear through opening 14 of the anchor 12 by partially attaching the anchor 12 to the outer covering 16 along reversible attachment line RAL via reversible fastener 40.

As compared to the variations of ear protector 10 shown in FIGS. 15-17, the variations of ear protector 10 shown in FIGS. 18-20 may facilitate relatively easier grasping of the ear helix H, and/or the portion of the anchor 12 that sits in proximity to the helix H, during passage of the wearer's ear through opening 14 of the anchor. In the variations of FIGS. 18-20, the outer covering 16 is positioned relatively distant from the wearer's ear helix H during passage of the wearer's ear through the opening 14. Such relative distance between the outer covering and the wearer's ear helix H in the open configuration may facilitate relatively easier passage of the wearer's ear through the opening 14.

7. Communication Elements

Ear protectors in accordance with the present invention may comprise one or more integrated or component communication elements 100 for transmitting, receiving and/or recording aural and/or visual information, e.g., audio, pictures and/or video. Such communication elements may comprise, for example, miniaturized speakers (e.g., headphones, earphones and/or ear buds), hearing aids, microphones, audio recorders, music/audio players, Point-of-View ("PoV") video recorders, 3-D video recorders, cameras, video players, audio/video recorders or players, audio/video receivers or transmitters, radios, telephones, mobile phones, video viewing devices, displays, information displays, digital displays, LCD displays, LED displays, OLED displays, plasma displays, heads-up displays, computers, combinations thereof, etc. These communication elements may couple to or communicate with one or more internal or external apparatus, such as music/audio/video players, (mobile) phones, memory devices (e.g., flash memory, solid state memory, hard drives, disc drives, etc.), communication networks, and/or computers. Communication may be provided via direct wire attachment and/or via wireless transmission and/or reception utilizing a wireless communication standard, such as Bluetooth®, Wi-Fi, GSM, 3GPP LTE, UMTS, CDMA, W-CDMA, TD-SCDMA, HSPA, HSPA+, TS-CDMA, EDGE, 1G, 2G, 3G, 4G, WiMAX, etc.

Figure 21:
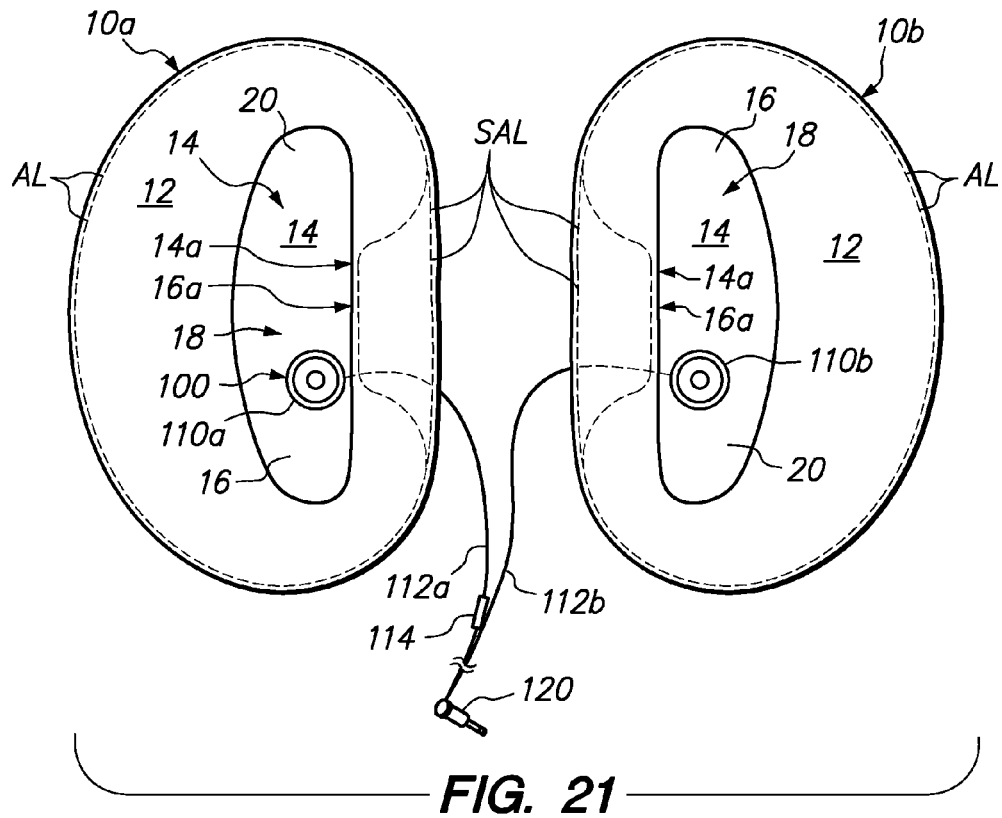
FIG. 21 is a schematic view illustrating an embodiment of the ear protector of FIG. 2 comprising one or more communication elements.

FIG. 21 illustrates an embodiment of ear protector 10 comprising communication element(s) 100. As seen in FIG. 21, a pair of ear protectors 10a and 10b comprise communication element(s) 100 with headphone speakers or other audio amplification/output devices (e.g., hearing aids) 110a and 110b, respectively, positioned within chamber 18 near anchor opening 14. Headphone speakers 110a and 110b comprise wires 112a and 112b, respectively, that extend from the headphone speakers to jack 120, which is configured to couple to or communicate with external apparatus, such as a music/audio/video player and/or recorder, a (mobile) phone and/or a computer. Element 100 also may comprise optional microphone or other audio recording device 114, e.g., positioned along wire 112a and/or 112b. In a variation of communication element(s) 100 of FIG. 21, the headphone speakers 110 may be hardwired to external apparatus, e.g., jack 120 may be eliminated such that wires 112 are permanently electrically coupled to the external apparatus.

In another variation, the communication element(s) of FIG. 21 may be wireless (i.e., the communication element(s) may omit wire(s) for coupling to external apparatus). In such a variation, the communication element(s) optionally may comprise one or more integrated internal apparatus, such as a (digital) audio player (e.g. an MPEG or AAC audio player), a hearing aid and/or a telephone (note that wired variations of communication element(s) 100 also may comprise such integrated internal apparatus). Additionally or alternatively, communication element(s) 100 of FIG. 21 may comprise a wireless transmitter/receiver for wirelessly communicating and exchanging data with external apparatus (see, e.g., FIG. 22).

Figure 22:
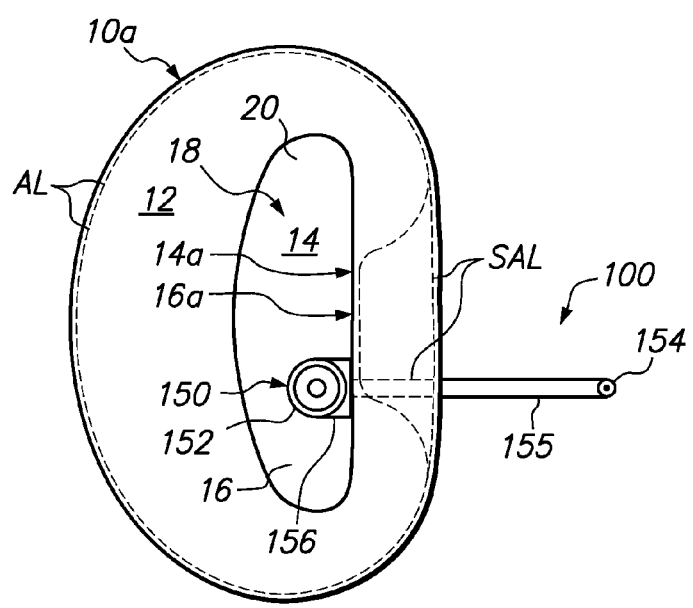
FIG. 22 is a schematic view of a variation of the ear protector of FIG. 21.

FIG. 22 illustrates a variation of ear protectors 10 of FIG. 21 comprising communication element(s) 100 having a wireless headset 150 with a headphone speaker or hearing aid 152 and a microphone 154. Headphone speaker 152 is positioned within chamber 18 of ear protector 10 near anchor opening 14 and may be connected to microphone 154 via extender 155. Optionally, microphone 154 additionally or alternatively may comprise a PoV camera and/or (digital) audio/video recording and/or viewing device(s). Optionally, an audio player, such as an MPEG or AAC audio player, and/or an audio/video player may be integrated into the wireless communication element(s) 100.

The wireless headset 150 optionally comprises a wireless transmitter/receiver 156 (or, alternatively, an optional independent wireless transmitter and independent wireless receiver) for wirelessly sending data to, and/or wirelessly receiving data from (e.g., sending/receiving audio and/or video input/output data), external apparatus. Microphone and optional PoV camera and/or audio/video device 154, as well as speaker 152, may be connected to the wireless transmitter/receiver 156 for communicating with the external apparatus. In a variation of the communication element(s) 100 of FIG. 22, headset 150 may comprise a wired headset having one or more wires, such as wires 112 of FIG. 21, for coupling to and communicating with the external apparatus.

Optionally, communication element(s) 100 (e.g., headphone speakers/hearing aids 110, wires 112, microphone 114, and/or jack 120 of FIG. 21; and/or headset 150, speaker/hearing aid 152, microphone and optional PoV camera and/or audio/video device 154, extender 155, and/or wireless transmitter/receiver 156 of FIG. 22) may be attached to ear protector 10, e.g., may be attached to anchor 12, outer covering 16 and/or to material layer(s) 20. Additionally or alternatively, the communication element(s) may be sandwiched between material layer(s) 20 and outer covering 16 or anchor 12, and/or may be sandwiched between the outer covering 16 and the anchor 12 (for example, in FIG. 22 the extender 155 illustratively is sandwiched between anchor 12 and outer covering 16 along a portion of its length along second attachment line SAL). Such attachment and/or sandwiching of communication element(s) 100 may stabilize the communication element(s) and/or may properly position the communication element(s) relative to the wearer's ear(s), eye(s), mouth and/or PoV. For example, such attachment and/or sandwiching may stabilize and/or properly position speaker(s) and/or other audio output/amplifying devices relative to the wearer's ear(s), may stabilize and/or properly position microphone(s) and/or other audio recording/amplifying device(s) relative to the wearer's mouth, may stabilize and/or properly position audio/video recording device(s) relative to the wearer's PoV, and/or may stabilize and/or properly position video viewing device(s) or display(s) relative to the wearer's eye(s).

8. Active Thermal Elements

Ear protectors in accordance with the present invention may comprise one or more integrated or component active thermal elements for actively heating or cooling the ear. Such active thermal elements may comprise, for example, thermoelectric elements, Peltier heaters/coolers, heat exchangers, resistive heaters, inductive heaters/coolers, chemical heaters, catalytic burners, fuel-based heaters, platinum catalyst heaters, charcoal burners, air-activated heaters, iron oxide heaters, calcium oxide heaters, crystallization-type heaters, supersaturated solution heaters, sodium acetate heaters, magnesium/copper sulfate heaters, air bladder heaters/coolers, fluid (e.g., water) bladder heaters/coolers, etc. These active thermal elements may couple to, or be integrated with, ear protectors of the present invention. In some variations, the active thermal elements may be reusable or rechargeable. In some variations, the active thermal elements may be one-time use, or may be fully or partially disposable. In some variations, the active thermal elements may comprise off-the-shelf active thermal elements that may be utilized in combination with ear protectors of the present invention.

Figures 23A, 23B:
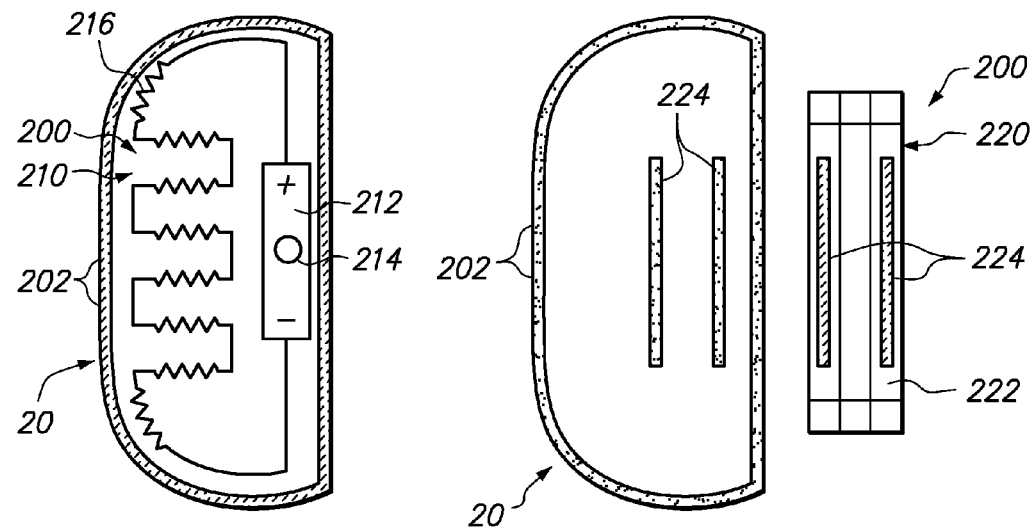
FIGS. 23A-23C are schematic views illustrating embodiments of the ear protector of FIG. 2 comprising one or more active thermal elements.
Figure 23C:
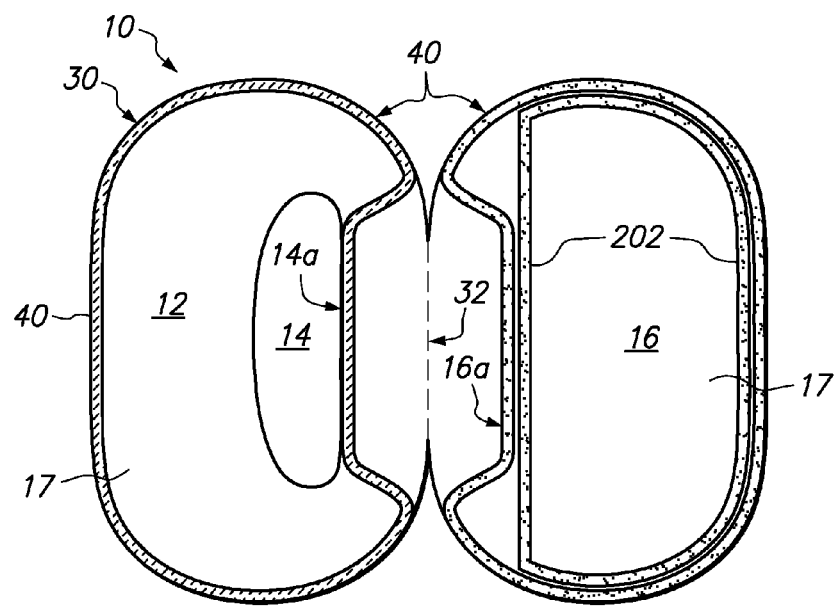

FIGS. 23A-23C illustrate representative embodiments of ear protector 10 and active thermal element 200. An active thermal element 200 optionally may be sandwiched between material layer 20 and outer covering 16 (and/or between material layer 20 and anchor 12) during use, as in the embodiments of FIG. 23. In the embodiments of FIG. 23, material layer 20 is configured for selective attachment and/or removal from ear protector 10 via reversible fastener 202 that is positioned on the material layer (see FIGS. 23A and 23B) and/or on the outer covering 16 (see FIG. 23C). As will be apparent, the portion of reversible fastener 202 positioned on outer covering 16 (and/or on anchor 12) for selective attachment of material layer 20 to the outer covering (and/or to the anchor) optionally may be integrated with the outer covering's (anchor's) reversible fastener 40 and/or with the outer covering's (anchor's) backing material 17 (e.g., previously described loop-type or unbreakable loop-type "UBL" backing material 17) that is used for selective attachment of the anchor 12 to the outer covering 16 during formation of chamber 18.

Reversible fastener 202 (illustratively a hook-and-loop fastener, though any other reversible fastener may be utilized) may facilitate access to active thermal element 200 before, during, or after use. Such access to the active thermal element 200 may, for example, facilitate activation, reloading, recharging, and/or power supply (battery) changing of the active thermal element. It should be understood that access to the active thermal element alternatively may be provided by any of a variety of alternative techniques. For example, material layer 20 may be permanently attached to the outer covering 16 along a portion of its outer perimeter, but may comprise a pouch (e.g., a segment of the material layer's outer perimeter may be unattached or reversibly attached to the outer covering) for accessing the active thermal element 200 sandwiched between material layer 20 and the outer covering 16. Additional access techniques will be apparent. In FIG. 23, the active thermal element is attached or integrated into the material layer 20, though it should be understood that the active thermal element 200 additionally or alternatively may be attached or integrated into the anchor 12 and/or the outer covering 16 of the ear protector 10.

As seen in FIG. 23A, in one variation active thermal element 200 may comprise resistive heater 210. Resistive heater 210 includes power supply 212 with positive and negative terminals, controller 214, and resistive wire 216. Power supply 212 may comprise, for example, one or more batteries, such as watch batteries, button cell batteries, coin cell batteries, disposable batteries, rechargeable batteries, Alkaline batteries, Silver batteries, Zinc-air batteries, Mercury batteries, Lithium batteries, Lithium-ion batteries, NiCd batteries, etc. Controller 214 controls the flow of current across resistive wire 216 and may comprise a temperature controller and/or a simple On/Off switch or button. Resistive wire 216 is attached to the positive and negative terminals of power supply 212 and may comprise any suitable single- or multi-stranded resistive wire, such as copper wire and/or stainless steel wire. Optionally, the resistive wire 216 may be sandwiched between material layer 20 and another material layer (not shown), or between two additional layer (not shown), such that the wearer can access the controller 214 and/or power supply 212, but not the resistive wire 216. This may reduce a risk of wire breakage and/or unintentional burns.

During use, resistive heater 210 of FIG. 23A may be activated via controller 214. Material layer 20 may be coupled to outer covering 16 of ear protector 10 shown in FIG. 23C via reversible fastener 202, which sandwiches the resistive heater 210 between the material layer 20 and the outer covering 16. Optionally, controller 214 may be operable by the wearer for activating or deactivating the resistive heater 210 while the heater is sandwiched between material layer 20 and outer covering 16, without necessitating temporary removal of the material layer from the outer covering. Ear protector 10 with activated resistive heater 210 may be attached to the wearer's ear (see, for example, FIG. 19), and the wearer's ear then is actively heated via the resistive heater. After use, the ear protector 10 may be removed from the wearer's ear, and the resistive heater may be deactivated via controller 214. Power supply 212 (e.g., batteries) optionally may be recharged or replaced prior to future use.

As seen in FIG. 23B, in another variation active thermal element 200 may comprise chemical heater 220. In FIG. 23B, chemical heater 220 illustratively comprises air-activated heater 222, such as an iron oxide heater, though it should be understood that any other chemical heater may be utilized, such as a crystallization-type supersaturated solution heater (e.g., a sodium acetate heater). Chemical heater 220 optionally may be sandwiched between material layer 20 and outer covering 16 of ear protector 10 without any additional attachment to the material layer or to the outer covering. Alternatively, the chemical heater may be permanently or reversibly attached to the material layer or to the outer covering. For example, the chemical heater 220 may comprise a single-use adhesive strip for temporarily attaching the heater to the material layer 20 or to the outer covering 16. Alternatively, as seen in FIG. 23B, the chemical heater 220 and the material layer 20 (or the outer covering 16) may comprise reversible fastener 224, illustratively a hook-and-loop fastener though any other reversible fastener may be utilized, for temporarily attaching the chemical heater to the ear protector.

During use, chemical heater 220 of FIG. 23B may be activated and optionally may be attached (e.g., via reversible fastener 224) to material layer 20 and/or to ear protector 10. Material layer 20 may be coupled to outer covering 16 of ear protector 10 shown in FIG. 23C via reversible fastener 202, which sandwiches the chemical heater 220 between the material layer 20 and the outer covering 16. Ear protector 10 with activated chemical heater 220 may be attached to the wearer's ear (see, for example, FIG. 19), and the wearer's ear then is actively heated via the chemical heater. After use, the ear protector 10 may be removed from the wearer's ear, and the chemical heater optionally may be recharged (e.g., when reusable) or replaced (e.g., when disposable) prior to future use.

Attaching material layer 20 to outer covering 16 (and/or anchor 12) via reversible fastener 202 (optionally including backing material 17, e.g., loop-type or unbreakable loop-type "UBL" backing material 17) facilitates use of various material layers 20 and/or active thermal elements 200 in combination with ear protector 10. This may facilitate use of material layers and/or active thermal elements of varying thermal properties dependent on the conditions for which ear protection is sought. For example, when used on a relatively warm day, a relatively thin or light or non-insulating material layer 20, or no material layer, may be utilized in combination with ear protector 10. On a cooler day, a more insulating material layer 20 and/or an active thermal element 200 may be utilized in combination with the ear protector. On a wet day, a waterproof material layer 20 may be utilized, a warmer active thermal element 200 may be utilized, etc. Any combination of material layer(s) 20 and/or active thermal element(s) 200 may be utilized, as desired.

9. Ear Protectors With Anterior-Projecting Flaps

As discussed previously, anchor 12 of ear protector 10 may comprise flap 15 that during use may be folded back towards or upon anchor 12 in the vicinity of lateral portion 14a of the opening 14, such that the opening is unobstructed and the flap is positioned against the wearer's head outside of chamber 18 of ear protector 10. In such a configuration, the flap may extend or project towards the anterior of the wearer's head (i.e., may extend towards the wearer's face), away from (e.g., generally perpendicular to) the tragus of the wearer's ear. When folded back towards or upon anchor 12 in this manner, flap 15 may resiliently press against the wearer's head in a manner that forms at least a partial seal. This seal may partially or completely block the elements, e.g., heat, cold, wind, rain and/or snow, from uncomfortably impinging upon the wearer's auricula A and/or entering the wearer's external acoustic meatus EAM. This seal may also reduce or eliminate previously described air gaps that allow some amount of wind and/or other elements to impinge on the ear. Furthermore, flap 15 may facilitate placement and/or removal of the ear protector by providing a surface that may be grasped during placement and/or removal.

Figure 24A:
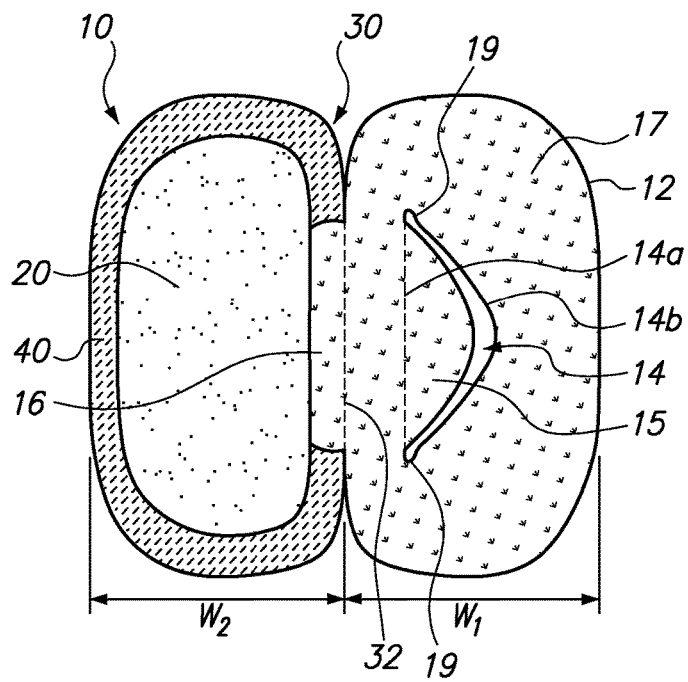
FIGS. 24A and 24B are schematic views illustrating an embodiment of the ear protector of FIG. 2 comprising a flap of material that projects anterior during use.

FIG. 24 illustrate an embodiment of ear protector 10 with such a flap of material 15 that during use is configured to extend or project towards the anterior of the wearer's head, generally away from and/or perpendicular to the tragus of the wearer's ear. As seen in FIG. 24A, ear protector 10 comprises anchor 12 having opening 14 and flap 15, and further comprises outer covering 16. Flap 15 may be connected to (e.g., may be formed as a unitary element with, or may be secondarily attached to) opening 14 of anchor 12 along all or a segment of lateral portion 14a of the opening 14, but may be (die-, laser-, etc.-) cut, stamped or otherwise detached from, or left unattached to, the cranial portion 14b of the opening 14. Ear protector 10 illustratively comprises minor axis symmetry (i.e., symmetry along the minor axis when the ear protector is in the closed configuration seen in FIG. 25B, which is the axis that generally extends anterior-posterior along the wearer's head during use); it should be understood that ear protector embodiments lacking minor axis symmetry, e.g., embodiments comprising a profile generally conforming to or mimicking the geometry or outer perimeter of the auricula A, alternatively may be provided.

Anchor 12 (including opening 14 and, optionally, flap 15) and outer covering 16 of ear protector 10 optionally may be fabricated as a unitary element on a single piece of foamed elastomer 30 (e.g., may be mechanically-, thermally-, fluidically-, water jet-, laser-, die- and/or otherwise cut or stamped from a sheet of foamed elastomer). The conforming anchor 12 and outer covering 16 may, for example, meet or interface along segment 32 of the single piece 30, which may serve as a hinge along which the single piece 30 may be folded back upon itself to approximate all or a portion of the outer perimeters of the anchor 12 and outer covering 16. Reversible fastener 40 is positioned along reversible attachment line RAL for reversibly fastening the outer covering 16 to the anchor 12 when single piece 30 is folded along segment 32, in order to form chamber 18. Optionally, when folded along segment 32, the single piece 30 may be permanently or reversibly secured to itself (e.g., via sewing, top stitching, gluing, bonding, hook-and-loop fastening, etc.) at or near the segment 32 and/or along an anterior portion of the attachment line, such that ear protector 10 is maintained in a partially open and partially closed configuration when the anchor 12 is not reversibly attached to the outer covering 16 along reversible attachment line RAL via reversible attachment 40 (in such a configuration, the anchor 12 and the outer covering 16 are nearly approximated, but chamber 18 is not fully formed such that the helix H and/or lobule L of the wearer's ear may be grasped during passage of the wearer's auricula A through opening 14).

In the embodiment of FIG. 24, backing material 17 applied to the interior surface of single piece 30 (i.e., the surface in proximity to the wearer's ear within chamber 18 during use of ear protector 10) illustratively comprises the loop component of a hook-and-loop fastener, while reversible fastener 40 illustratively comprises the hook component of the hook-and-loop fastener (e.g., a Velcro® fastener, marketed by Velcro Industries B.V. of Amsterdam, The Netherlands). The hook component reversible fastener 40 illustratively is attached (e.g., sewn, glued, bonded or otherwise connected) to outer covering 16 along the outer covering's interior surface between the ends of segment 32 and along reversible attachment line RAL (e.g., along the outside edge or perimeter of the outer covering). The reversible fastener 40 is configured to reversibly engage and attach to the interior surface backing material 17 when single piece 30 is folded over upon itself along segment 32 in order to reversibly fasten the outer covering 16 to the anchor 12 along the reversible attachment line RAL, thereby forming ear protector 10 with chamber 18.

Interior surface backing material 17 may, for example, comprise a loop-type or an unbreakable loop-type ("UBL") backing material. Optionally, the interior surface backing material 17 may comprise a low profile loop-type or UBL backing material. Likewise, the hook component reversible fastener 40 optionally may comprise a low profile or molded hook-type fastener, such as an Ultra-Mate® Velcro® fastener (Velcro Industries B.V., Amsterdam, The Netherlands). A low profile or molded hook-and-loop fastener may provide a smoother interface as compared to standard hook-and-loop fasteners, which may be more comfortable should backing material 17 or reversible fastener 40 come into contact with the wearer's ear or head.

As will be apparent, in a variation of the embodiment of FIG. 24, the reversible fastener 40 may be attached to the interior surface of the anchor 12 between the ends of segment 32 along reversible attachment line RAL, rather than to the interior surface of the outer covering 16. In another variation, backing material 17 may comprise the hook component of the hook-and-loop fastener, while reversible fastener 40 may comprise the loop component of the hook-and-loop fastener. In another variation, the reversible fastener 40 may comprise both the hook and loop components of the hook-and-loop fastener: in such a variation, the hook component may be attached to the interior surface of the outer covering 16 along reversible attachment line RAL, while the loop component may be attached to the interior surface of anchor 12 along reversible attachment line RAL (or vice versa). In yet another variation, reversible fastener 40 may comprise a reversible fastener other than a hook-and-loop reversible fastener, for example, button(s), zipper(s), hook(s), snap(s), or any other reversible fastener(s), as desired.

As discussed previously, ear protector 10 optionally may comprise one or more material layers 20 that are reversibly or permanently attached to the anchor 12 and/or the outer covering 16, e.g., to enhance insulation of chamber 18 from ambient conditions, to provide a desired texture at the interface between the ear protector 10 and the wearer's ear within chamber 18, to enhance weather protection/waterproofing, etc. Material layer(s) 20 may be attached to any surface of ear protector 10, as desired, and preferably are attached to the interior surface(s) disposed within chamber 18 during use at or near the interface with the wearer's ear. Exemplary material layers 20 include, for example, fleece, wool, insulation (e.g., Thinsulate® marketed by 3M Corporation of St. Paul, Minn.), fabric protectors, polytetrafluoroethylene (e.g., Teflon® marketed by DuPont of Wilmington, Del.), denim, fur, leather, suede, velvet, faux fur, faux leather (e.g., vinyl), faux suede, combinations thereof, etc. Previously described communication element(s) 100 and/or active thermal element(s) 200 also optionally may be provided (see FIGS. 21-23), e.g., may be attached to (and/or sandwiched between) material layer(s) 20, outer covering 16 and/or anchor 12.

In the embodiment of FIG. 24, ear protector 10 illustratively comprises material layer(s) 20 attached to the interior surface of outer covering 16. The material layer(s) may, for example, be inset relative to reversible fastener 40 positioned along the reversible attachment line RAL, or may be sandwiched between the reversible fastener 40 and the outer covering 16 along the reversible attachment line RAL (e.g., the reversible fastener 40 may be reversibly or permanently attached to the material layer(s) 20, which may be reversibly or permanently attached to the outer covering 16). Furthermore, material layer(s) 20 may be configured for selective attachment and/or removal from ear protector 10, e.g., via previously described reversible fastener 202 that may be positioned on the material layer(s) 20 (see FIGS. 23A and 23B) and/or on the outer covering 16 (see FIG. 23C). As previously discussed, the portion of reversible fastener 202 positioned on outer covering 16 (and/or on anchor 12) for selective attachment of material layer(s) 20 to the outer covering (and/or to the anchor) optionally may be integrated with the outer covering's (anchor's) reversible fastener 40 and/or with the outer covering's (anchor's) interior surface backing material 17 (e.g., previously described loop-type or unbreakable loop-type "UBL" backing material 17) that is used for selective attachment of the anchor 12 to the outer covering 16 during formation of chamber 18.

In some embodiments of ear protector 10, it may be desirable to provide the anchor 12 and the outer covering 16 with different maximum dimensions or widths along the ear protector's minor axis (i.e., the minor axis when the ear protector is in its closed configuration having chamber 18, which is the axis that generally extends anterior-posterior along the wearer's head during use). The anchor and outer covering additionally or alternatively may comprise different maximum dimensions or lengths along the ear protector's major/superior-inferior axis, or may comprise any other varying geometry as desired. In some embodiments, it may be desirable to provide the anchor 12 with a relatively greater maximum dimension/width while providing the outer covering 16 with a relatively lesser maximum dimension/width along the minor axis, since, during use, the anchor may need to conform to or traverse a relatively wider or more tortuous cranial surface of the wearer's auricula A, while the outer covering may need to conform to or traverse a relatively narrower or less tortuous lateral surface of the wearer's auricula A along the auricula's anterior-posterior axis.

In the embodiment of FIG. 24, anchor 12 comprises a minor axis maximum dimension or width $W_1$, while outer covering 16 comprises a minor axis maximum dimension or width $W_2$. As best seen in the open configuration of ear protector 10 shown in FIG. 24A, anchor width $W_1$ optionally may be greater than outer covering width $W_2$. Providing anchor 12 with a relatively greater maximum dimension or width along the minor axis than the maximum dimension or width of outer covering 16 along the minor axis may accommodate different cranial and lateral surface morphology of the auricula A while facilitating proper sizing and placement of the ear protector 10. For example, such varied minor axis maximum dimensions/widths may facilitate proper alignment of the anchor 12 and the outer covering 16 for attachment along reversible attachment line RAL during use. It should be understood that any ear protector embodiment of the present invention, including all previously described embodiments of ear protector 10, optionally may comprise varying geometry between the anchor and the ear protector, e.g., may comprise a greater minor axis maximum dimension/width anchor in combination with a lesser minor axis maximum dimension/width outer covering.

Figure 24B:
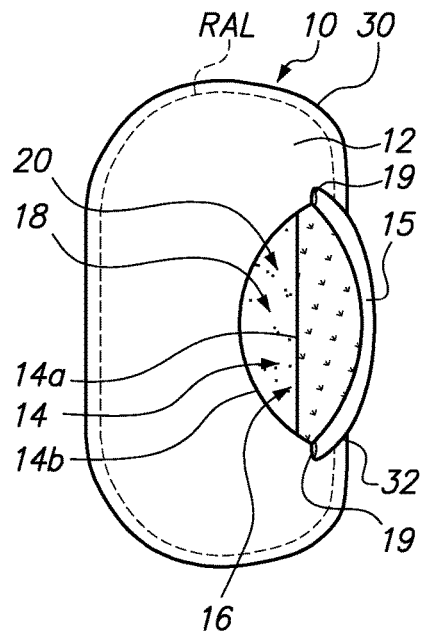

As discussed previously, in the closed configuration of ear protector 10 (e.g., after single piece 30 has been folded over upon itself along segment 32, and anchor 12 has been reversibly fastened to outer covering 16 via reversible fastener 40 along reversible attachment line RAL to form chamber 18, as in FIG. 24B), the minor axis maximum dimension or width of the ear protector 10 preferably may be in the range of about 1.5 inches to 3 inches (e.g., in the range of about 4 cm to 8 cm), and more preferably in the range of about 1.5 inches to 2.5 inches (e.g., in the range of about 4 cm to 7 cm). Anchor width $W_1$ and outer covering width $W_2$ also may be within these ranges, while anchor width $W_1$ optionally may be about 0-0.5 inches (e.g., about 0-1.3 cm) greater than outer covering width $W_2$. More preferably, anchor width $W_1$ may be about 0-0.25 inches (e.g., about 0-0.65 cm) greater than outer covering width $W_2$. In one embodiment, ear protector 10 and anchor 12 may comprise a common minor axis maximum dimension or width $W_1$ of about 2 inches (e.g., about 5.1 cm), while outer covering 16 may comprise a relatively smaller minor axis maximum dimension or width $W_2$ of about 1.875 inches (e.g., about 4.75 cm).

In order to provide ear protector 10 with an aesthetically pleasing profile, all or a portion of the edge of foamed elastomer single piece 30, anchor 12, opening 14, flap 15, outer covering 16, material layer(s) 20, and/or reversible fastener(s) 40 optionally may be finished. Finishing may comprise, for example, attaching edging material, binding tape, and/or stitching to all or a portion of the edge. Finishing via stitching or sewing may comprise, for example, one or more of top stitching, Serger stitching, 3-thread Serger stitching, 4-thread Serger stitching, overlock stitching, Merrow® machine (Merrow Sewing Machine Co., Fall River, Mass.) stitching, button hole stitching, and/or embroidery stitching. Aesthetic designs, patterns, logos, etc., additionally or alternatively may be provided on any internal or external surface of ear protector 10, for example, may be attached, sewn, glued, embroidered, woven, silkscreened, embossed, rubber embossed, heat embossed, printed, painted, flocked, transferred, or otherwise provided on the ear protector. It should be understood that finished edges and/or aesthetic designs, patterns, logos, etc., optionally may be provided with any ear protector of the present invention, including any previously described embodiment of ear protector 10.

In the embodiment of FIG. 24, opening 14 illustratively comprises optional pressure adjusters 19, illustratively shown as pressure adjusters positioned along the superior and inferior ends of the lateral portion 14*a* of the opening 14. Pressure adjusters 19 may accommodate selective excess expansion of opening 14 during use of ear protector 10 with ears having relatively large ear roots R, which may facilitate more comfortable and secure resilient engagement of opening 14 with a broader range of ear root geometries or sizes. For example, the pressure adjusters 19 may allow use of ear protector 10 with a relatively large ear root R without significantly increased pressure resiliently applied to the ear root R by the additional expansion of the opening 14 required to accommodate the relatively large ear root R. Likewise, the pressure adjuster may allow use of the ear protector with a relatively small ear root R without significantly reduced pressure resiliently applied to the ear root R due to opening 14 being oversized in order to accommodate relatively large ear roots R. Furthermore, pressure adjusters 19 may facilitate more comfortable placement and/or removal of ear protector 10 by facilitating excess expansion of the opening 14 during passage of the external ear auricula A through the opening.

Although pressure adjusters 19 illustratively are shown along both the superior and inferior ends of the lateral portion 14*a* of the opening 14, it should be understood that a pressure adjuster 19 optionally may be provided only along the superior end or only the inferior end of the lateral portion 14*a* of the opening 14. Pressure adjuster(s) 19 additionally or alternatively may be provided at any other location, as desired, around the perimeter of opening 14. Furthermore, although pressure adjusters 19 illustratively are shown in combination with flap 15, it should be understood that pressure adjusters may be provided with embodiments of ear protector 10 that do not comprise flap 15. One or more pressure adjusters optionally may be provided with any ear protector of the present invention, for example, with any of the previously described embodiments of the ear protector 10.

As seen in FIG. 24B, when ear protector 10 is in the closed configuration, flap 15 may project or extend at an angle relative to anchor 12 and outer covering 16. This projection angle may provide access to opening 14 during placement of the wearer's ear through the opening, may facilitate anterior extension or projection of the flap along wearer's head during use, and/or may facilitate grasping of flap 15 for simplifying placement and/or removal of the ear protector 10 (see FIG. 25).

Referring now to FIG. 25, a method of using the ear protector of FIG. 24 is described. As seen in FIG. 25A, ear protector 10 optionally may be placed in a partially open and partially closed configuration, wherein an anterior portion of the anchor 12 has been approximated with an anterior portion of the outer covering 16 via folding of single piece 30 over upon itself along segment 32. Such partial approximation of the anterior portions of the anchor and the outer covering optionally may be maintained by reversibly or permanently attaching the approximated anterior portions of the anchor and outer covering to one another. For example, the approximated anterior portions of the anchor and outer covering may be reversibly attached to one another near segment 32 of single piece 30 along an anterior portion of the reversible attachment line RAL via reversible fastener 40 (e.g., via engagement of hook component reversible fastener 40 with loop component interior surface backing material 17). Alternatively, the approximated anterior portions may be permanently attached to one another, e.g., by sewing, gluing, bonding and/or otherwise permanently attaching the approximated anterior portions to one another, for example, in the vicinity of/along segment 32 of single piece 30 and/or along the anterior portion of the attachment line located near segment 32. Although, in FIG. 25, ear protector 10 is placed in a partially open and partially closed configuration during passage of the wearer's external ear auricula A through opening 14, it should be understood that ear protector 10 alternatively may be positioned over the wearer's auricula A while the ear protector is in the fully open configuration of FIG. 24A.

Figure 25A:
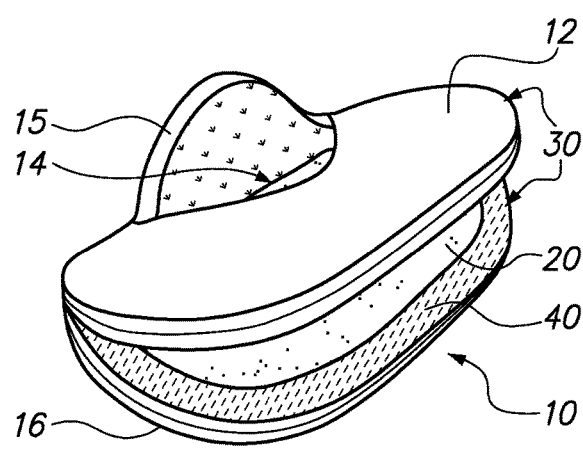
FIGS. 25A-25G are schematic views illustrating a method of using the ear protector of FIG. 24.
Figure 25B:
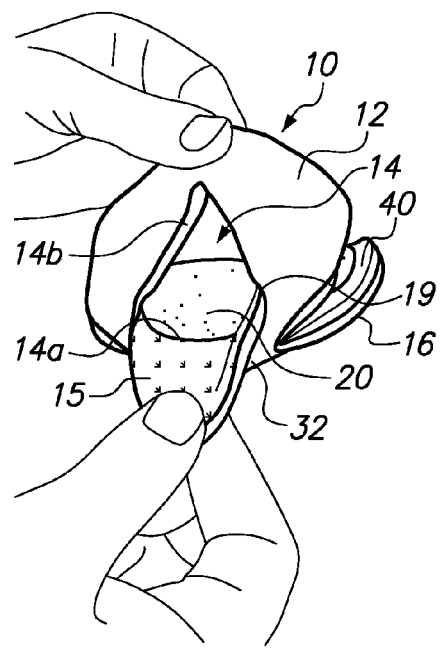

As seen in FIG. 25B, in order to place the partially (or fully) open ear protector 10 over the wearer's ear, the wearer may grasp flap 15 with the thumb and finger(s) of one hand, while grasping a posterior portion of the anchor 12 (i.e., a portion of the anchor configured for placement in proximity to the cranial surface of the wearer's ear) with the thumb and finger(s) of his/her other hand. The thumb grasping the flap preferably grasps the interior surface of the flap (i.e., the surface placed in proximity to the wearer's head/cheek during use), while the other finger(s) grasping the flap preferably grasp the flap's exterior surface. The thumb grasping the anchor preferably grasps the exterior surface of the anchor (i.e., the surface facing the wearer's head during use), while the other finger(s) grasping the anchor preferably grasp the anchor's interior surface (i.e., the anchor surface configured for placement in proximity to the cranial surface of the wearer's ear). The wearer preferably does not grasp the unattached posterior portion of outer covering 16.

Since the embodiment of ear protector 10 shown in FIGS. 24 and 25 illustratively comprises minor axis symmetry, it may be worn on either the right or left ear. When worn on the wearer's left ear, flap 15 may be grasped with the wearer's right hand, while anchor 12 may be grasped with the wearer's left hand during placement of the ear protector on the wearer's left ear. When worn on the wearer's right ear, flap 15 may be grasped with the wearer's left hand, while anchor 12 may be grasped with the wearer's right hand during placement of the ear protector on the wearer's right ear. Thus, the hand corresponding to the ear on which the ear protector 10 is to be worn may grasp the anchor 12, while the opposite hand may grasp flap 15. FIG. 25 illustratively show placement of ear protector 10 on the wearer's left ear, i.e., show grasping of flap 15 with the wearer's right hand and grasping of anchor 12 with the wearer's left hand.

Figure 25C:
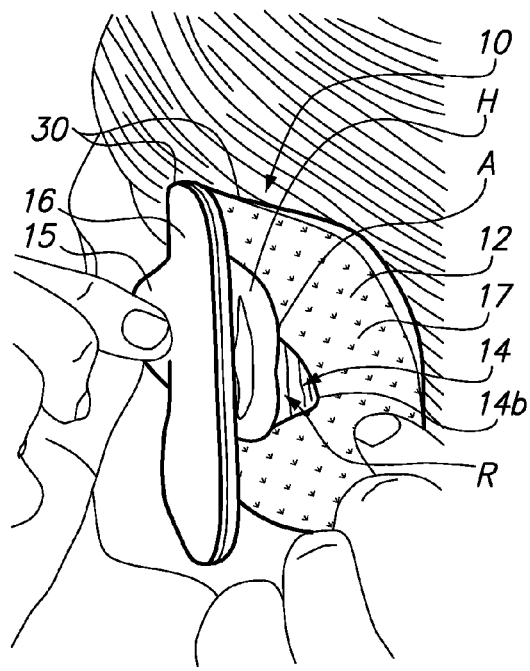

As seen in FIG. 25B, with ear protector 10 grasped as described, opening 14 may be resiliently deformed or widened by pulling flap 15 away from anchor 12. This may provide additional space for passage of the wearer's ear through the opening and may also remove flap 15 as an obstruction across opening 14. As seen in FIG. 25C, the helix H of the wearer's ear may be passed through opening 14 while flap 15 is pulled anterior and anchor 12 is pulled posterior. In this manner, flap 15 may serve as an ear protector placement/removal facilitator that facilitates placement and/or removal of the ear protector 10 on/from the wearer's ear. Flap 15 may be partially or completely folded towards or against anchor 12 in the vicinity of lateral portion 14a of opening and may at least partially seal against the wearer's head/cheek in a manner that reduces or eliminates air gaps and/or at least partially blocks the elements during use.

Figure 25D:
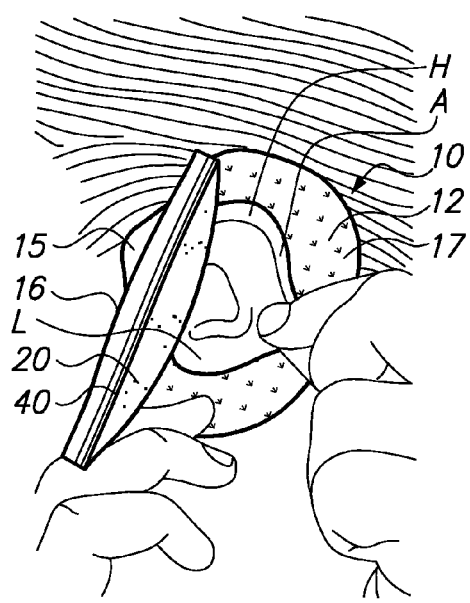

Once helix H has been passed through the opening 14 of ear protector 10, with flap 15 extending or projecting anterior of the wearer's tragus T in the direction of the wearer's face, the wearer's hands may be repositioned to complete passage of auricula A through the opening. As seen in FIG. 25D, the hand that had been grasping the flap may, for example, be repositioned to grasp an inferior portion of the anchor 12, while the hand that had been grasping the anchor may be repositioned to grasp wearer's ear, e.g., the helix H and/or lobule L of the wearer's ear. While holding the ear protector 10 relatively stationary with the hand grasping the inferior portion of the anchor 12, the hand grasping the wearer's ear (e.g., grasping helix H and/or lobule L) may pull or otherwise urge the helix and/or lobule superior and/or posterior in order to pull or otherwise urge the remainder of helix H and/or lobule L through opening 14 in order to complete passage of the auricula A through the opening.

Figure 25E:
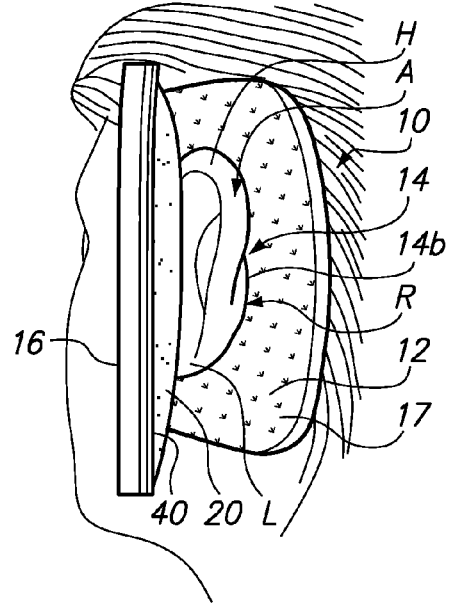

As seen in FIG. 25E, with the auricula A passed through the opening 14 and the wearer releasing the auricula A and the ear protector 10, opening 14 spontaneously conforms to all or a portion of the geometry of the ear root R in order to securely and comfortably maintain the ear protector 10 in position over the external ear auricula A without additional external support. Lateral portion 14a of the opening is placed in proximity to the ear root R along the lateral surface of the ear (e.g., along the origin of tragus T), while cranial portion 14b is placed in proximity to the ear root R along the cranial surface of the ear (e.g., along the origins of the cartilage of meatus CM and eminentia conchae EC). Flap 15 generally extends or projects anterior relative to the wearer's head, e.g., generally extends perpendicular or away from the wearer's tragus T.

Figure 25F:
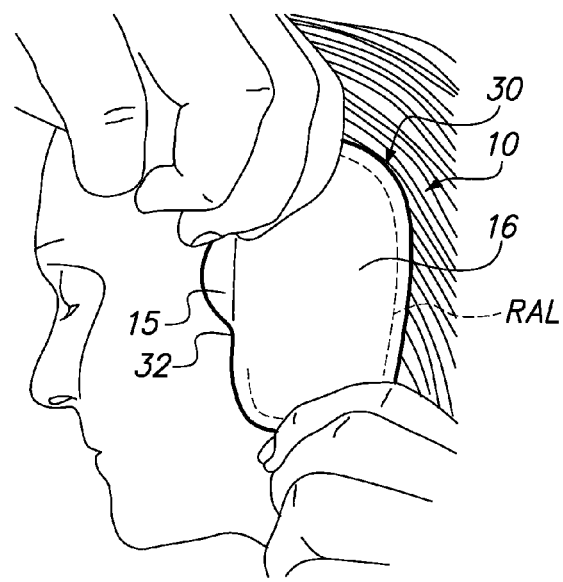

As seen in FIG. 25F, after completing passage of the auricula A through the opening 14, the wearer may use one or both hands to fully approximate any un-approximated portions of the outer perimeters of anchor 12 and outer covering 16 (e.g., the posterior portions of their outer perimeters, which are in proximity to the wearer's ear helix H) along reversible attachment line RAL via reversible fastener 40, thereby fully forming ear protector 10 with chamber 18 containing the wearer's auricula A. Before or after formation of chamber 18, the wearer optionally may grasp the flap 15 and the anchor 12 (and/or the outer covering 16) in order to rotate or otherwise make fine adjustments to the position of the flap 15 and the ear protector 10 relative to the auricula A passed through the opening.

Figure 25G:
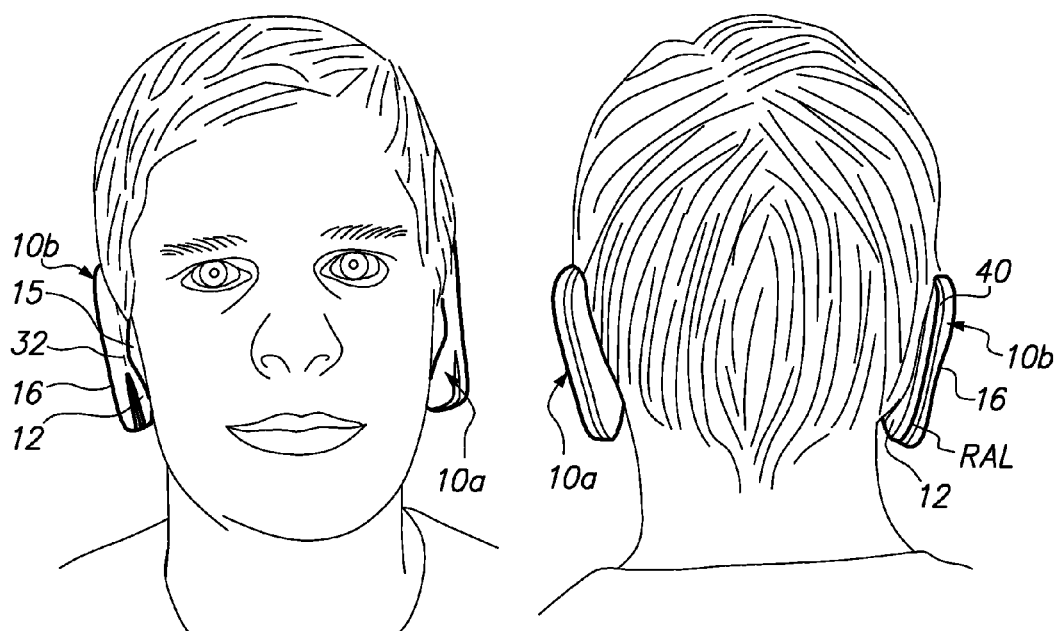

The wearer also may grasp flap 15 and anchor 12/outer covering 16 during removal of the ear protector, e.g. after use. For example, the flap may be pulled anterior while the remainder of the ear protector is pulled posterior in order to resiliently deform and/or widen opening 14 during removal of the wearer's auricula A from chamber 18 via reverse passage of the auricula A through the opening 14. Optionally, anchor 12 and outer covering 16 may be partially or fully detached from one another along reversible attachment line RAL (e.g., by undoing reversible fastener 40) during or after removal of auricula A from the ear protector 10. Ear protector placement and/or removal optionally may be repeated with a second protector 10 placed on the wearer's opposite ear. FIG. 25G shows ear protectors 10a and 10b placed on the wearer's left and right ears, respectively.

During use, ear protector 10 protects auricula A from the elements, and flap 15 resiliently presses against the wearer's head or cheek in a manner that forms at least a partial seal. This seal may partially or completely eliminate air gaps and block the elements, e.g., heat, cold, wind, rain and/or snow, from uncomfortably impinging upon the wearer's auricula A and/or entering the wearer's external acoustic meatus EAM.

III. Conclusion

Although preferred illustrative embodiments and variations of methods and apparatus of the present invention are described above, it will be apparent to those skilled in the art that various changes and modifications may be made thereto without departing from the invention. As an example, although the methods and apparatus for ear protection generally have been described during use with ears comprising detached, unattached or free lobules L, it should be understood that the methods and apparatus of the present invention additionally or alternatively may be used with the less common ears comprising attached lobules L (i.e., lobules that are at least partially attached to the head). When utilized in combination with an ear having an attached lobule L, a portion of the auricula A in the vicinity of the lobule optionally may remain outside of chamber 18 during use of the ear protector 10, and/or the geometry of opening 14 optionally may be altered to accommodate the different geometry of the ear root R. As another example, the ear protectors 10 described herein may be used in conjunction with, or integrated into, helmets of various sorts. Such helmets may comprise, for example, athletic helmets, work helmets, safety helmets, skiing helmets, snowboarding helmets, skateboarding helmets, inline skating helmets, bicycling helmets, equestrian helmets, football helmets, hockey helmets, baseball helmets, polo helmets, rock climbing helmets, hang gliding helmets, surfing helmets, kayaking helmets, sailing helmets, boating helmets, motorcycling helmets, car racing helmets, hard hats, combinations thereof, etc. It is intended in the appended claims to cover all such changes and modifications that fall within the true spirit and scope of the invention.

What is claimed is:

1. An ear protector for an external ear comprising:
   an anchor fabricated from a closed cell foamed elastomer, the anchor having a perimeter and an opening located interior to the perimeter, the opening having a resiliently deformable edge and extending through the closed cell foamed elastomer, the anchor configured to conformably engage at least a portion of a root of the external ear when the external ear is passed through the opening;
   a flap of material configured to extend anterior to the external ear to at least partially block ambient conditions from impinging on the external ear when the external ear is disposed through the opening, the flap integral to the anchor and having upper and lower ends defining a lateral portion axis and a shape complementary to the resiliently deformable edge of the opening such that the flap is configured to hinge at the lateral portion axis to permit the opening to be occluded or exposed based on the position of the flap; such that the flap is configured to occlude the opening and mate with the resiliently deformable edge of the opening when the external ear is not disposed through the opening; and
   an insulating outer covering configured to mate with the anchor along the perimeter to create a chamber that encloses the external ear when the external ear is disposed through the opening.

2. The ear protector of claim 1, wherein the anchor and the insulating outer covering are fabricated as a single piece of closed cell foamed elastomer with the anchor and the outer covering connected to one another along at least one segment of the single piece.

3. The ear protector of claim 1, wherein the flap further is configured to facilitate placement or removal of the ear protector.

4. The ear protector of claim 1, wherein the ear protector comprises minor axis symmetry.

5. The ear protector of claim 1, wherein the anchor has a perimeter adapted to conform to an outer perimeter of the external ear.

6. The ear protector of claim 1 further comprising at least one bistable ear clamp coupled to the anchor,
   wherein the at least one bistable ear clamp is configured to evert to clamp the external ear within the chamber between the ear clamp and the insulating outer covering when the opening conformably engages at least a portion of the external ear root.

7. The ear protector of claim 1 further comprising at least one element chosen from the group consisting of communication elements, active thermal elements, and combinations thereof.

8. The ear protector of claim 1, wherein the insulating outer covering is flexible.

9. The ear protector of claim 1, wherein the anchor is configured to be self-supporting when engaged on the external ear.

10. The ear protector of claim 1, further comprising an additional layer of insulating material disposed on a side of the insulating outer covering that is configured to mate with the anchor.

11. A method for protecting an external ear, the method comprising:
    providing an ear protector comprising an insulating outer covering, a closed cell foamed elastomer anchor having a perimeter and an opening having a resiliently deformable edge and extending through the anchor located interior to the perimeter, and a flap of material configured to extend anterior to the external ear to at least partially block ambient conditions from impinging on the external ear when the external ear is disposed through the opening, the flap integral to the anchor and having upper and lower ends defining a lateral portion axis and a shape complementary to the resiliently deformable edge of the opening such that the flap is configured to hinge at the lateral portion axis to permit the opening to be occluded or exposed based on the position of the flap; such that the flap is configured to occlude the opening and mate with the resiliently deformable edge of the opening when the external ear is not disposed through the opening;
    passing the external ear through the opening such that the opening of the anchor conformably engages at least a portion of a root of the external ear; and
    attaching the anchor to the insulating outer covering along the perimeter to create a chamber accessible through the opening and configured to receive the external ear through the opening.

12. The method of claim 11, wherein attaching the anchor to the insulating outer covering along the perimeter is at least partially reversible to selectively define the chamber.

13. The method of claim 11, wherein providing an ear protector further comprises providing a bistable ear clamp that is coupled to the anchor and that is configured to evert to clamp the external ear between the ear clamp and the insulating outer covering.

14. The method of claim 11 further comprising transmitting, receiving, broadcasting, displaying, amplifying, playing, or recording aural or visual information via at least one communication element integrated into or coupled to the ear protector.

15. The method of claim 11, wherein providing an ear protector further comprises providing at least one active thermal element that is configured to heat or cool the external ear.

16. An ear protector for an external ear comprising:
    an anchor fabricated from a foamed elastomer, the anchor having a perimeter and an opening located interior to the perimeter, the opening having a resiliently deformable edge and extending through the foamed elastomer, the anchor configured to conformably engage at least a portion of a root of the external ear when the external ear is passed through the opening;
    a flap of material configured to extend anterior to the external ear to at least partially block ambient conditions from impinging on the external ear when the external ear is disposed through the opening, the flap integral to the anchor and having upper and lower ends defining a lateral portion axis and a shape complementary to the resiliently deformable edge of the opening such that the flap is configured to hinge at the lateral portion axis to permit the opening to be occluded or exposed based on the position of the flap; such that the flap is configured to occlude the opening and mate with the resiliently deformable edge of the opening when the external ear is not disposed through the opening; and an insulating outer covering configured to at least partially mate with the anchor along the perimeter via a reversible fastener to create a chamber that encloses the external ear when the external ear is disposed through the opening, the reversible fastener chosen from the group consisting of hook-and-loop fasteners, buttons, zippers, hooks, snaps and combinations thereof.

17. The ear protector of claim 16, wherein the anchor is configured to be self-supporting when engaged on the external ear.

18. The ear protector of claim 16, further comprising an additional layer of insulating material disposed on a side of the insulating outer covering that is configured to mate with the anchor.

\* \* \* \* \*